(12) United States Patent
Mohandas

(10) Patent No.: US 11,222,031 B1
(45) Date of Patent: Jan. 11, 2022

(54) DETERMINING TERMINOLOGIES FOR ENTITIES BASED ON WORD EMBEDDINGS

(71) Applicant: Ciitizen, LLC, San Francisco, CA (US)

(72) Inventor: Gokhuldass Mohandas, Palo Alto, CA (US)

(73) Assignee: Ciitizen, LLC, San Francisco, CA (US)

(*) Notice: Subject to any disclaimer, the term of this patent is extended or adjusted under 35 U.S.C. 154(b) by 220 days.

(21) Appl. No.: 16/565,250

(22) Filed: Sep. 9, 2019

(51) Int. Cl.
*G06F 16/30* (2019.01)
*G06F 16/2458* (2019.01)
*G16H 10/60* (2018.01)
*G06F 16/33* (2019.01)
*G06F 40/30* (2020.01)

(52) U.S. Cl.
CPC ........ *G06F 16/2465* (2019.01); *G06F 16/334* (2019.01); *G06F 40/30* (2020.01); *G16H 10/60* (2018.01)

(58) Field of Classification Search
CPC .... G06F 16/2465; G06F 16/334; G06F 40/30; G16H 10/60
See application file for complete search history.

(56) References Cited

U.S. PATENT DOCUMENTS

| | | | |
|---|---|---|---|
| 11,030,999 B1* | 6/2021 | Yu ................ | G10L 15/1815 |
| 2017/0011289 A1* | 1/2017 | Gao ................ | G06F 40/268 |
| 2017/0270100 A1* | 9/2017 | Audhkhasi ........ | G06F 40/289 |
| 2018/0157644 A1* | 6/2018 | Mandt .............. | G06N 20/00 |
| 2020/0035228 A1* | 1/2020 | Seo ................. | G06F 40/295 |

OTHER PUBLICATIONS

Article entitled "Evaluation of Word Embedding Vector Averaging Functions for Biomedical Word Sense Disambiguation", by Antunes et al., dated 2017 (Year: 2017).*
Article entitled "A Supervised Learning Approach for ICU Mortality Predication based on Unstructured Electrocardiogram Text Reports", by Krishnan et al., dated 2018 (Year: 2018).*
Article entitled "Augmenting Word Embeddings through External Knowledge-base for Biomedical Application", by Jha et al., dated 2017 (Year: 2017).*
Article entitled "Retrofitting Word Embeddings with the UMLES Metathesaurus for Clinical Information Extraction", by Alawad et al., dated 2018 (Year: 2018).*

* cited by examiner

*Primary Examiner* — Mahesh H Dwivedi
(74) *Attorney, Agent, or Firm* — Sterne, Kessler, Goldstein & Fox P.L.L.C.

(57) ABSTRACT

Some embodiments provide a program that receives a set of words. The program further determines an embedding for a word in the set of words. The program also accesses a knowledge base to retrieve a plurality of entries. Each entry includes a text description of a concept. The program further determines, for each entry in the plurality of entries in the knowledge base, an embedding for the entry based on the text description of the concept. The program also calculates, for each entry in the plurality of entries in the knowledge base, a distance value between the embedding for the word in the set of words and the embedding for the entry. The program further determines an entry in the plurality of entries in the knowledge base having a text description of a concept that best represents the set of words based on the plurality of distance values.

17 Claims, 29 Drawing Sheets

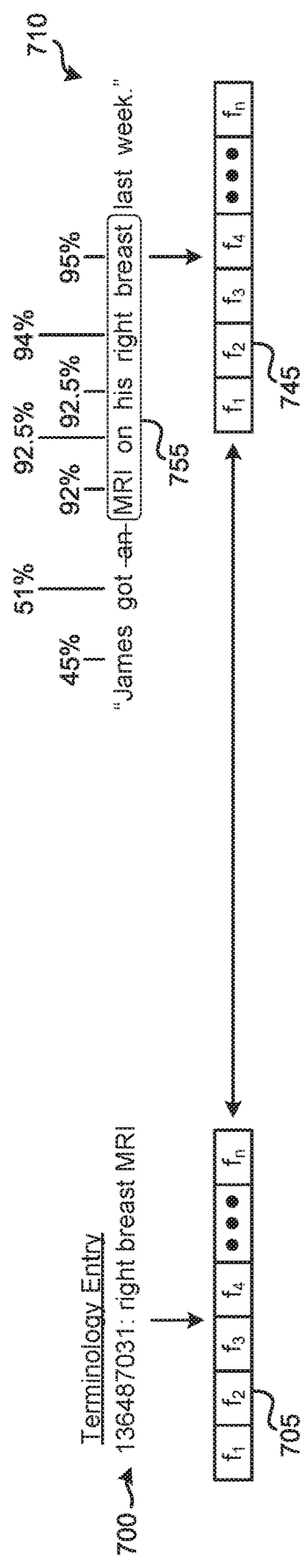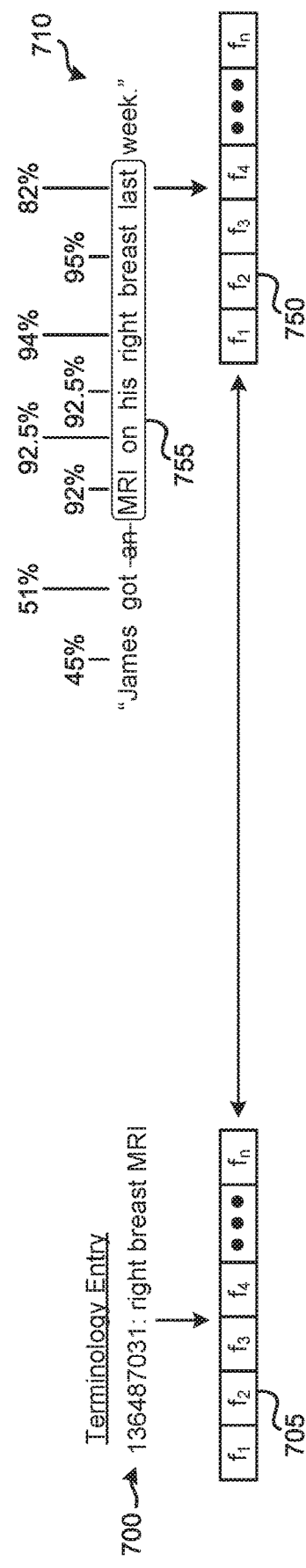
FIG. 7G
FIG. 7H

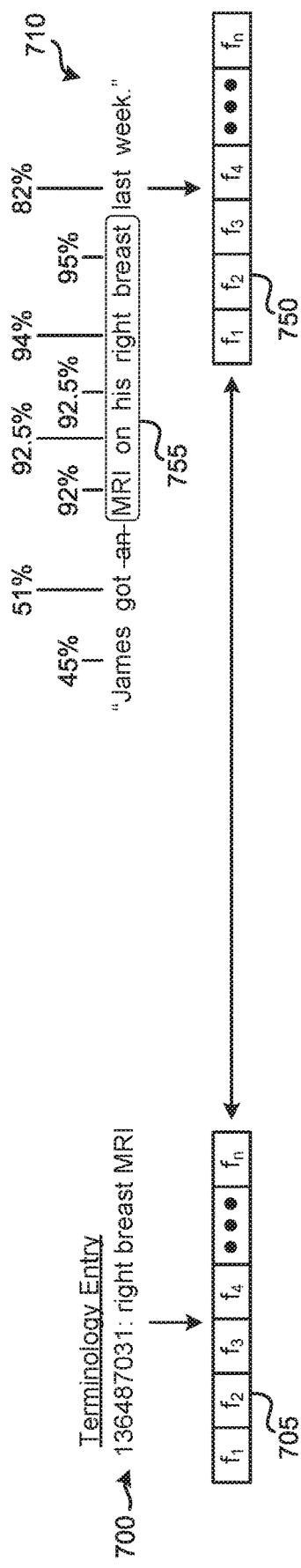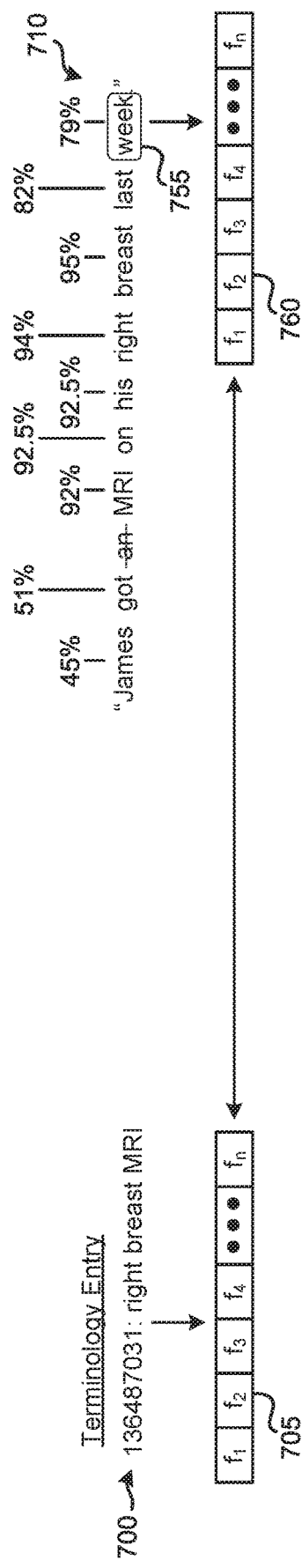
FIG. 7I
FIG. 7J

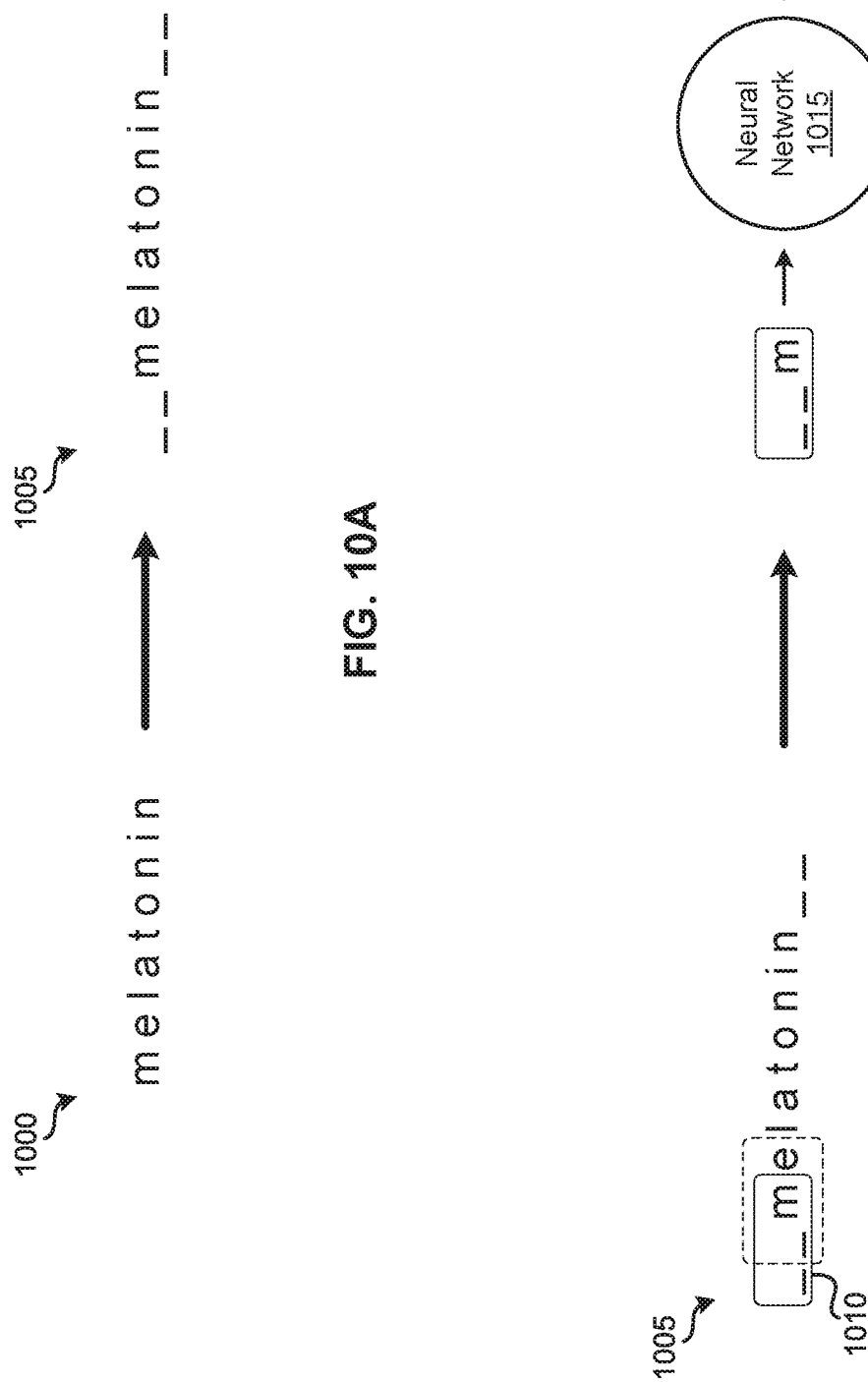

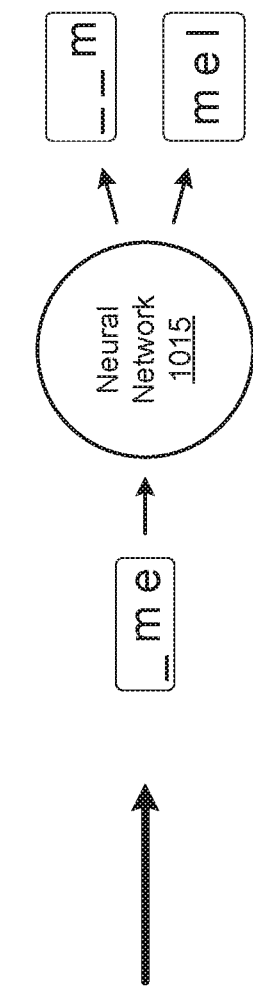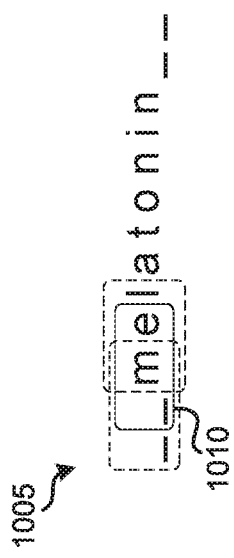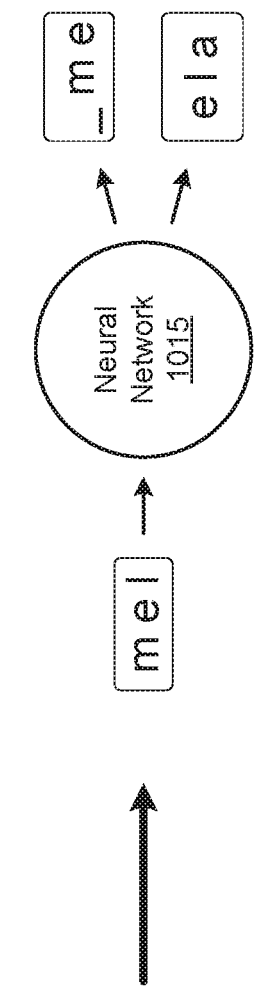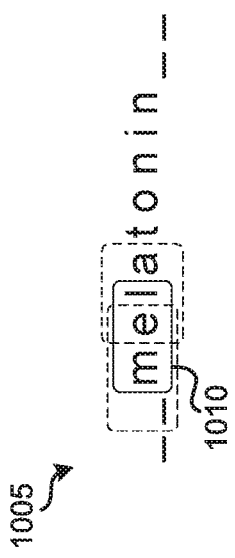
FIG. 10C
FIG. 10D

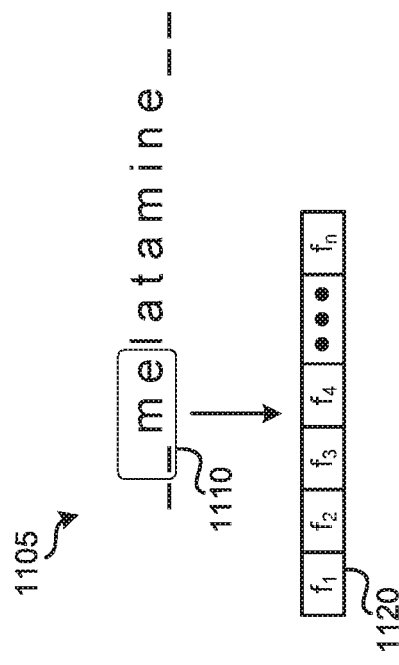
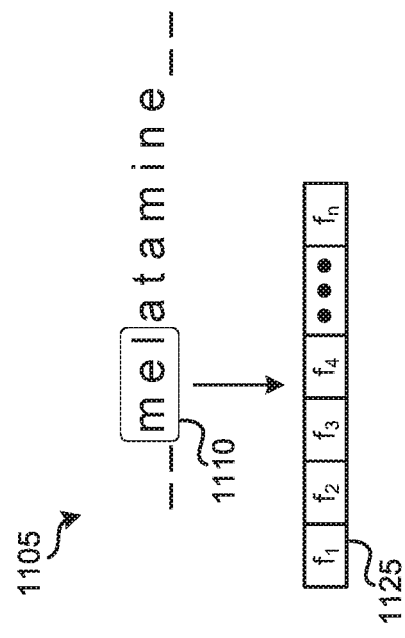
FIG. 11C
FIG. 11D

DETERMINING TERMINOLOGIES FOR ENTITIES BASED ON WORD EMBEDDINGS

BACKGROUND

Word embedding is a technique for representing words using vector representations in a vector space. The position of a particular word in the vector space may be learned from neighboring words surrounding the particular word (i.e., its context) in a corpus of text. As such, words that are used in similar ways in the corpus of text will likely have similar vector representations in the vector space. The position of a particular word in the learned vector space can be referred to as the embedding of the word. Several methods may be used to learn word embeddings. For example, a Word2Vec methodology, which uses predictive models, can be used to learn word embeddings. As another example, a GloVe methodology, which uses count-based models, may be used to learn word embeddings. Once learned, word embeddings have numerous applications. For instance, they can be used for sentiment analysis, document classification, syntactic parsing, etc.

SUMMARY

In some embodiments, a non-transitory machine-readable medium stores a program executable by at least one processing unit of a device. The program receives a set of words. The program further determines an embedding for a word in the set of words. The program also accesses a knowledge base to retrieve a plurality of entries. Each entry includes a text description of a concept. The program further determines, for each entry in the plurality of entries in the knowledge base, an embedding for the entry based on the text description of the concept. The program also calculates, for each entry in the plurality of entries in the knowledge base, a distance value between the embedding for the word in the set of words and the embedding for the entry. The program further determines an entry in the plurality of entries in the knowledge base having a text description of a concept that best represents the set of words based on the plurality of distance values.

In some embodiments, the determined distance value may be a first distance value. The program may further select a defined number of entries from the plurality of entries in the knowledge base having the shortest distance value, determine a subset of the set of words, generate an embedding for the subset of the set of words, and calculate, for each entry in the defined number of entries, a second distance value between the embedding for the subset of the set of words and the embedding for the entry. Determining the entry in the plurality of entries in the knowledge base having the text description of the concept that best represents the set of words based on the plurality of first distance values may include determining the entry in the plurality of entries in the knowledge base having the text description of the concept that best represents the set of words based on the plurality of first distance values and the plurality of second distance values.

In some embodiments, determining, for each entry in the plurality of entries in the knowledge base, the embedding for the entry based on the text description of the concept may include determining an embedding for each word in a set of words in the description of the concept. The program may further generate, for each entry in the plurality of entries in the knowledge base, an embedding for the entry based on the determined embeddings for each word in the set of words in the description of the concept. Generating, for each entry in the plurality of entries in the knowledge base, the embedding for the entry may include calculating an average of the determined embeddings for each word in the set of words and using the average as the embedding for the entry.

In some embodiments, the determined entry in the plurality of entries in the knowledge base may be the entry having a shortest distance value. The knowledge base may be a medical terminology knowledge base. Each entry in the knowledge base may further include a unique identifier associated with the concept described by the text description. The set of words may be raw unstructured text from a document in a medical record of a patient.

In some embodiments, a method receives a set of words. The method further determines an embedding for a word in the set of words. The method also accesses a knowledge base to retrieve a plurality of entries. Each entry includes a text description of a concept. The method further determines, for each entry in the plurality of entries in the knowledge base, an embedding for the entry based on the text description of the concept. The method also calculates, for each entry in the plurality of entries in the knowledge base, a distance value between the embedding for the word in the set of words and the embedding for the entry. The method further determines an entry in the plurality of entries in the knowledge base having a text description of a concept that best represents the set of words based on the plurality of distance values.

In some embodiments, the determined distance value may be a first distance value. The method may further select a defined number of entries from the plurality of entries in the knowledge base having the shortest distance value, determine a subset of the set of words, generate an embedding for the subset of the set of words, and calculate, for each entry in the defined number of entries, a second distance value between the embedding for the subset of the set of words and the embedding for the entry. Determining the entry in the plurality of entries in the knowledge base having the text description of the concept that best represents the set of words based on the plurality of first distance values may include determining the entry in the plurality of entries in the knowledge base having the text description of the concept that best represents the set of words based on the plurality of first distance values and the plurality of second distance values In some embodiments, determining, for each entry in the plurality of entries in the knowledge base, the embedding for the entry based on the text description of the concept may include determining an embedding for each word in a set of words in the description of the concept. The method may further generate, for each entry in the plurality of entries in the knowledge base, an embedding for the entry based on the determined embeddings for each word in the set of words in the description of the concept. Generating, for each entry in the plurality of entries in the knowledge base, the embedding for the entry may include calculating an average of the determined embeddings for each word in the set of words and using the average as the embedding for the entry.

In some embodiments, the determined entry in the plurality of entries in the knowledge base may be the entry having a shortest distance value. The knowledge base may be a medical terminology knowledge base. Each entry in the knowledge base may further include a unique identifier associated with the concept described by the text description. The set of words may be raw unstructured text from a document in a medical record of a patient.

In some embodiments, a system includes a set of processing units and a non-transitory machine-readable medium that stores instructions. The instructions cause at least one processing unit to receive a set of words. The instructions further cause the at least one processing unit to determine an embedding for a word in the set of words. The instructions also cause the at least one processing unit to access a knowledge base to retrieve a plurality of entries. Each entry includes a text description of a concept. The instructions further cause the at least one processing unit to determine, for each entry in the plurality of entries in the knowledge base, an embedding for the entry based on the text description of the concept. The instructions also cause the at least one processing unit to calculate, for each entry in the plurality of entries in the knowledge base, a distance value between the embedding for the word in the set of words and the embedding for the entry. The instructions further cause the at least one processing unit to determine an entry in the plurality of entries in the knowledge base having a text description of a concept that best represents the set of words based on the plurality of distance values.

In some embodiments, the determined distance value may be a first distance value. The instructions may further cause the at least one processing unit to select a defined number of entries from the plurality of entries in the knowledge base having the shortest distance value, determine a subset of the set of words, generate an embedding for the subset of the set of words, and calculate, for each entry in the defined number of entries, a second distance value between the embedding for the subset of the set of words and the embedding for the entry. Determining the entry in the plurality of entries in the knowledge base having the text description of the concept that best represents the set of words based on the plurality of first distance values may include determining the entry in the plurality of entries in the knowledge base having the text description of the concept that best represents the set of words based on the plurality of first distance values and the plurality of second distance values.

In some embodiments, determining, for each entry in the plurality of entries in the knowledge base, the embedding for the entry based on the text description of the concept may include determining an embedding for each word in a set of words in the description of the concept. The instructions may further cause the at least one processing unit to generate, for each entry in the plurality of entries in the knowledge base, an embedding for the entry based on the determined embeddings for each word in the set of words in the description of the concept. Generating, for each entry in the plurality of entries in the knowledge base, the embedding for the entry may include calculating an average of the determined embeddings for each word in the set of words and using the average as the embedding for the entry.

In some embodiments, the determined entry in the plurality of entries in the knowledge base may be the entry having a shortest distance value. The knowledge base may be a medical terminology knowledge base. Each entry in the knowledge base may further include a unique identifier associated with the concept described by the text description.

In some embodiments, a non-transitory machine-readable medium stores a program executable by at least one processing unit of a device. The program receives a set of words. The program further retrieves an entry from a knowledge base comprising a plurality of entries. Each entry includes a text description of a concept. The program also determines an embedding for the entry based on the text description of the concept. The program further iteratively determines an embedding for a word in the set of words, increases a size of a window of words in the set of words, and calculates a confidence score for the entry with respect to the word based on the embedding for the entry and the embedding for words in the window of words until a successive calculated confidence score decreases below a previous calculated confidence score. The program also determines that a window of words in the set of words having a previous size represents an entity.

In some embodiments, determining the embedding for the entry based on the text description of the concept may include determining an embedding for each word in a set of words in the description of the concept. The program may further generate an embedding for the entry based on the determined embeddings for each word in the set of words. Generating the embedding for the entry may include calculating an average of the determined embeddings for each word in the set of words and using the average as the embedding for the entry.

In some embodiments, the program may further, before iteratively determining an embedding for a word in the set of words, increasing a size of a window of words in the set of words, and calculating a confidence score for the entry with respect to the word based on the embedding for the entry and the embedding for the words in the window of words, remove words from the set of words based on a list of stop words. The previous calculated confidence score may be calculated for the embedding for the window of words in the set of words having the previous size.

In some embodiments, the program may further set the size of the window of words to a default size and reset the size of the window of words to the default size when a particular calculated confidence score for a particular word is less than a defined threshold score. The knowledge base may be a medical terminology knowledge base. Each entry in the knowledge base may further include a unique identifier associated with the concept described by the text description.

In some embodiments, a method receives a set of words. The method further retrieves an entry from a knowledge base comprising a plurality of entries, each entry comprising a text description of a concept. The method also determines an embedding for the entry based on the text description of the concept. The method further iteratively determines an embedding for a word in the set of words, increases a size of a window of words in the set of words, and calculates a confidence score for the entry with respect to the word based on the embedding for the entry and the embedding for words in the window of words until a successive calculated confidence score decreases below a previous calculated confidence score. The method also determines that a window of words in the set of words having a previous size represents an entity.

In some embodiments, determining the embedding for the entry based on the text description of the concept may include determining an embedding for each word in a set of words in the description of the concept. The method may further generate an embedding for the entry based on the determined embeddings for each word in the set of words. Generating the embedding for the entry may include calculating an average of the determined embeddings for each word in the set of words and using the average as the embedding for the entry.

In some embodiments, the method may further, before iteratively determining an embedding for a word in the set of words, increasing a size of a window of words in the set of words, and calculating a confidence score for the entry with respect to the word based on the embedding for the entry and the embedding for the words in the window of words, remove words from the set of words based on a list of stop words. The previous calculated confidence score may be calculated for the embedding for the window of words in the set of words having the previous size.

In some embodiments, the method may further set the size of the window of words to a default size and reset the size of the window of words to the default size when a particular calculated confidence score for a particular word is less than a defined threshold score. The knowledge base may be a medical terminology knowledge base. Each entry in the knowledge base may further include a unique identifier associated with the concept described by the text description.

In some embodiments, a system includes a set of processing units and a non-transitory machine-readable medium that stores instructions. The instructions cause the at least one processing unit to receive a set of words. The instructions further cause the at least one processing unit to retrieve an entry from a knowledge base comprising a plurality of entries. Each entry includes a text description of a concept. The instructions also cause the at least one processing unit to determine an embedding for the entry based on the text description of the concept. The instructions further cause the at least one processing unit to iteratively determine an embedding for a word in the set of words, increase a size of a window of words in the set of words, and calculate a confidence score for the entry with respect to the word based on the embedding for the entry and the embedding for words in the window of words until a successive calculated confidence score decreases below a previous calculated confidence score. The instructions also cause the at least one processing unit to determine that a window of words in the set of words having a previous size represents an entity.

In some embodiments, determining the embedding for the entry based on the text description of the concept may include determining an embedding for each word in a set of words in the description of the concept. The instructions may further cause the at least one processing unit to generate an embedding for the entry based on the determined embeddings for each word in the set of words. Generating the embedding for the entry may include calculating an average of the determined embeddings for each word in the set of words and using the average as the embedding for the entry.

In some embodiments, the instructions may further cause the at least one processing unit to, before iteratively determining an embedding for a word in the set of words, increasing a size of a window of words in the set of words, and calculating a confidence score for the entry with respect to the word based on the embedding for the entry and the embedding for the words in the window of words, remove words from the set of words based on a list of stop words. The previous calculated confidence score may be calculated for the embedding for the window of words in the set of words having the previous size.

In some embodiments, the instructions may further cause the at least one processing unit to set the size of the window of words to a default size and reset the size of the window of words to the default size when a particular calculated confidence score for a particular word is less than a defined threshold score.

In some embodiments, a non-transitory machine-readable medium stores a program executable by at least one processing unit of a device. The program receives a set of words. The program further determines a first set of character embeddings for a first set of windows of characters in an unknown word in the set of words. The program also determines a first word embedding for the unknown word based on the first set of character embeddings. The program further determines a second set of character embeddings for a second set of windows of characters in a known word. The program also determines a second word embedding for the known word based on the second set of character embeddings. The program further determines a third word embedding for the unknown word based on the first word embedding for the unknown word and the second word embedding for the known word.

In some embodiments, the program may further detect the unknown word in the set of words. Detecting the unknown word in the set of words may include determining that the unknown word is a first word that is not included in a corpus of data used to train a neural network configured to train word embeddings for words in the corpus of data. The known word may be a second word that is included in the corpus of data used to train the neural network.

In some embodiments, the program may further determine an embedding for a subset of words in the set of words based on the word embedding for the unknown word. The unknown word may be included in the subset of the set of words. The program may further calculate an average of the word embedding for the unknown word and word embeddings for words in the subset of the set of words other than the unknown word and use the average as the embedding for the subset of the set of words.

In some embodiments, the program may further determine a fourth word embedding for the known word based on a word embedding space. Determining the third word embedding for the unknown word may include using the fourth word embedding for the known word as the third word embedding for the unknown word. Each window of characters in the first set of windows of characters and the second set of windows of characters may have a same size.

In some embodiments, a method receive a set of words. The method further determines a first set of character embeddings for a first set of windows of characters in an unknown word in the set of words. The method also determines a first word embedding for the unknown word based on the first set of character embeddings. The method further determines a second set of character embeddings for a second set of windows of characters in a known word. The method also determines a second word embedding for the known word based on the second set of character embeddings. The method further determines a third word embedding for the unknown word based on the first word embedding for the unknown word and the second word embedding for the known word.

In some embodiments, the method may further detect the unknown word in the set of words. Detecting the unknown word in the set of words may include determining that the unknown word is a first word that is not included in a corpus of data used to train a neural network configured to train word embeddings for words in the corpus of data. The known word may be a second word that is included in the corpus of data used to train the neural network.

In some embodiments, the method may further determine an embedding for a subset of words in the set of words based on the word embedding for the unknown word. The unknown word may be included in the subset of the set of words. The method may further calculate an average of the word embedding for the unknown word and word embeddings for words in the subset of the set of words other than the unknown word and use the average as the embedding for the subset of the set of words.

In some embodiments, the method may further determine a fourth word embedding for the known word based on a word embedding space. Determining the third word embedding for the unknown word may include using the fourth word embedding for the known word as the third word embedding for the unknown word. Each window of characters in the first set of windows of characters and the second set of windows of characters may have a same size.

In some embodiments, a system includes a set of processing units and a non-transitory machine-readable medium that stores instructions. The instructions cause the at least one processing unit to receive a set of words. The instructions further cause the at least one processing unit to determine a first set of character embeddings for a first set of windows of characters in an unknown word in the set of words. The instructions also cause the at least one processing unit to determine a first word embedding for the unknown word based on the first set of character embeddings The instructions further cause the at least one processing unit to determine a second set of character embeddings for a second set of windows of characters in a known word. The instructions also cause the at least one processing unit to determine a second word embedding for the known word based on the second set of character embeddings. The instructions further cause the at least one processing unit to determine a third word embedding for the unknown word based on the first word embedding for the unknown word and the second word embedding for the known word.

In some embodiments, the instructions may further cause the at least one processing unit to detect the unknown word in the set of words. Detecting the unknown word in the set of words may include determining that the unknown word is a first word that is not included in a corpus of data used to train a neural network configured to train word embeddings for words in the corpus of data. The known word may be a second word that is included in the corpus of data used to train the neural network.

In some embodiments, the instructions may further cause the at least one processing unit to determine an embedding for a subset of words in the set of words based on the word embedding for the unknown word. The unknown word may be included in the subset of the set of words. The instructions may further cause the at least one processing unit to calculate an average of the word embedding for the unknown word and word embeddings for words in the subset of the set of words other than the unknown word and use the average as the embedding for the subset of the set of words.

In some embodiments, the instructions may further cause the at least one processing unit to determine a fourth word embedding for the known word based on a word embedding space. Determining the third word embedding for the unknown word may include using the fourth word embedding for the known word as the third word embedding for the unknown word.

In some embodiments, a non-transitory machine-readable medium stores a program executable by at least one processing unit of a device. The program receives a plurality of sets of words. Each set of words in the plurality of sets of words includes a word annotated as being an entity having a same custom entity type. The program further determines a plurality of word embeddings in a word embedding space for the plurality of annotated words. The program also defines a region in the word embedding space based on the received plurality of word embeddings. The program further receives a set of words. The program also determines a word embedding for a subset of the set of words. The program further determines whether the word embedding falls within the defined region in the word embedding space. Upon determining that the word embedding falls within the defined region in the word embedding space, the program also determines that the subset of the set of words represents an entity having the custom entity type.

In some embodiments, the plurality of word embeddings may be a first plurality of word embeddings. The custom entity type may be a first custom entity type. The region in the word embedding space may be a first region in the word embedding space The program may further receive a second plurality of word embeddings in the word embedding space, where each word embedding in the second plurality of word embeddings is associated with a second custom entity type, and define a second region in the word embedding space based on the received second plurality of word embeddings. The entity may be a first entity. The program may further determine whether the word embedding falls within the second defined region in the word embedding space and, upon determining that the word embedding falls within the second defined region in the word embedding space, determine that the subset of the set of words represents a second entity having the second custom entity type.

In some embodiments, defining the region in the word embedding space may include generating a convex hull in the word embedding space based on the received plurality of word embeddings. Determining whether the word embedding falls within the defined region in the word embedding space may include determining whether the word embedding falls within a defined threshold distance of the convex hull. The set of words may include raw unstructured text from a document in a medical record of a patient. The set of words may include set of words included in a textual description of a concept for an entry in a knowledge base.

In some embodiments, a method receives a plurality of sets of words. Each set of words in the plurality of sets of words includes a word annotated as being an entity having a same custom entity type. The method further determines a plurality of word embeddings in a word embedding space for the plurality of annotated words. The method also defines a region in the word embedding space based on the received plurality of word embeddings. The method further receives a set of words. The method also determines a word embedding for a subset of the set of words. The method further determines whether the word embedding falls within the defined region in the word embedding space. Upon determining that the word embedding falls within the defined region in the word embedding space, the method also determines that the subset of the set of words represents an entity having the custom entity type.

In some embodiments, the plurality of word embeddings may be a first plurality of word embeddings. The custom entity type may be a first custom entity type. The region in the word embedding space may be a first region in the word embedding space. The method may further receive a second plurality of word embeddings in the word embedding space, where each word embedding in the second plurality of word embeddings is associated with a second custom entity type, and define a second region in the word embedding space based on the received second plurality of word embeddings. The entity may be a first entity. The method may further determine whether the word embedding falls within the second defined region in the word embedding space and, upon determining that the word embedding falls within the second defined region in the word embedding space, determine that the subset of the set of words represents a second entity having the second custom entity type.

In some embodiments, defining the region in the word embedding space may include generating a convex hull in the word embedding space based on the received plurality of word embeddings. Determining whether the word embedding falls within the defined region in the word embedding space may include determining whether the word embedding falls within a defined threshold distance of the convex hull. The set of words may include raw unstructured text from a document in a medical record of a patient. The set of words may include set of words included in a textual description of a concept for an entry in a knowledge base.

In some embodiments, a system includes a set of processing units and a non-transitory machine-readable medium that stores instructions. The instructions cause the at least one processing unit to receive a plurality of sets of words. Each set of words in the plurality of sets of words includes a word annotated as being an entity having a same custom entity type. The instructions further cause the at least one processing unit to determine a plurality of word embeddings in a word embedding space for the plurality of annotated words, The instructions also cause the at least one processing unit to define a region in the word embedding space based on the received plurality of word embeddings. The instructions further cause the at least one processing unit to receive a set of words. The instructions also cause the at least one processing unit to determine a word embedding for a subset of the set of words. The instructions further cause the at least one processing unit to determine whether the word embedding falls within the defined region in the word embedding space. Upon determining that the word embedding falls within the defined region in the word embedding space, the instructions also cause the at least one processing unit to determine that the subset of the set of words represents an entity having the custom entity type.

In some embodiments, the plurality of word embeddings may be a first plurality of word embeddings. The custom entity type may be a first custom entity type. The region in the word embedding space may be a first region in the word embedding space. The instructions may further cause the at least one processing unit to receive a second plurality of word embeddings in the word embedding space, where each word embedding in the second plurality of word embeddings is associated with a second custom entity type, and define a second region in the word embedding space based on the received second plurality of word embeddings. The entity may be a first entity. The instructions may further cause the at least one processing unit to determine whether the word embedding falls within the second defined region in the word embedding space and, upon determining that the word embedding falls within the second defined region in the word embedding space, determine that the subset of the set of words represents a second entity having the second custom entity type.

In some embodiments, defining the region in the word embedding space may include generating a convex hull in the word embedding space based on the received plurality of word embeddings. Determining whether the word embedding falls within the defined region in the word embedding space may include determining whether the word embedding falls within a defined threshold distance of the convex hull. The set of words may include raw unstructured text from a document in a medical record of a patient.

The following detailed description and accompanying drawings provide a better understanding of the nature and advantages of the present invention.

BRIEF DESCRIPTION OF THE DRAWINGS

FIGS. 7A-7J illustrate an example of recognizing an entity in raw text according to some embodiments.

FIGS. 10A-10H illustrate an example of training character embeddings according to some embodiments.

FIGS. 11A-11H illustrate an example of determining a word embedding for an unknown word based on character embeddings according to some embodiments.

DETAILED DESCRIPTION

Figure 1:
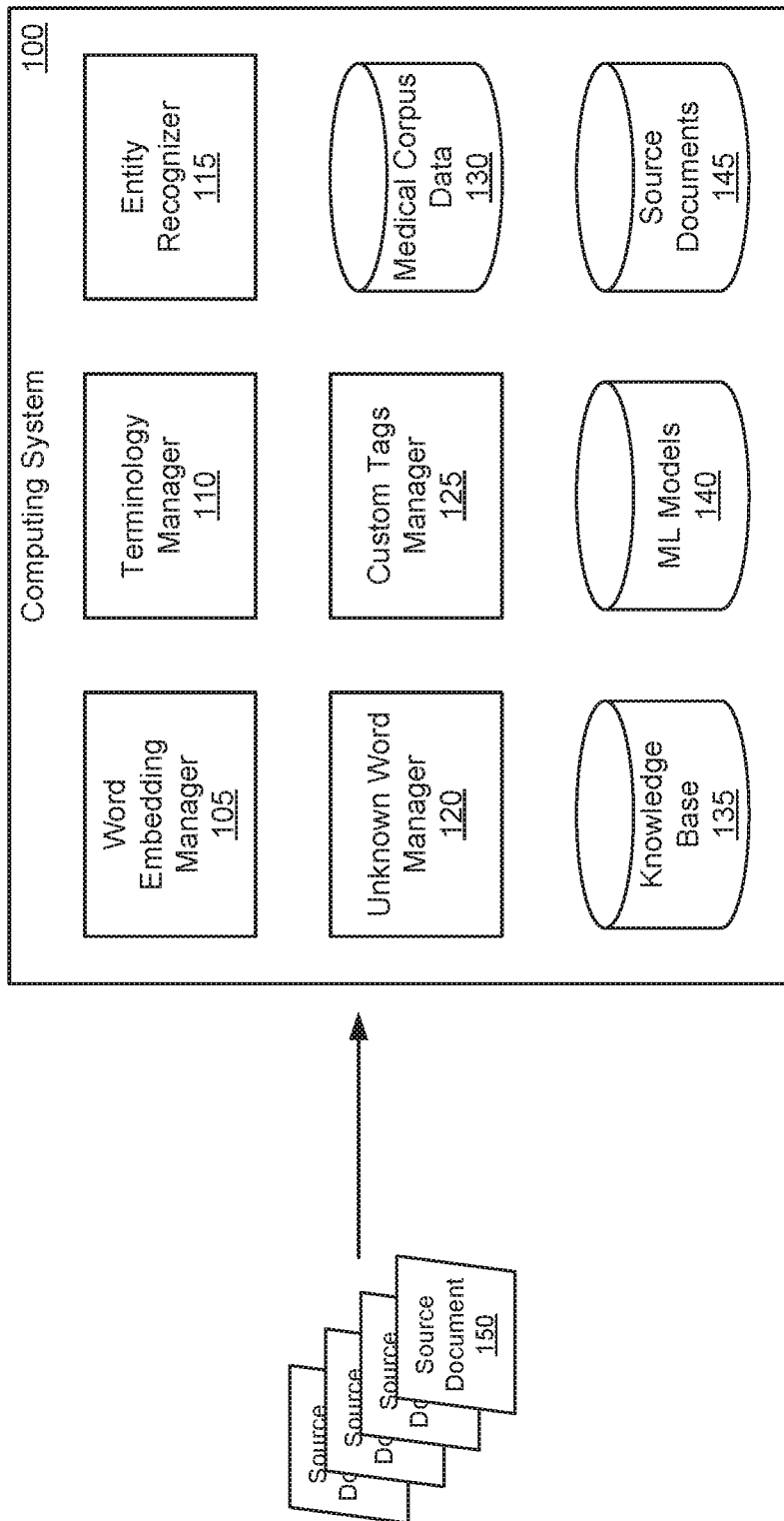
FIG. 1 illustrates a computing system that processes documents based on embeddings according to some embodiments.

In the following description, for purposes of explanation, numerous examples and specific details are set forth in order to provide a thorough understanding of the present invention. It will be evident, however, to one skilled in the art that the present invention as defined by the claims may include some or all of the features in these examples alone or in combination with other features described below, and may further include modifications and equivalents of the features and concepts described herein.

Described herein are several techniques for processing documents based on embeddings. In some embodiments, a computing system manages a knowledge base of standardized encodings of information. For example, each entry in the knowledge base can describe a particular concept and include a unique identifier (e.g., a unique code). The computing system may receive for processing source documents that contain raw and unstructured text. Next, the computing system uses any number of different methods for identifying entities in sequences of raw and unstructured text (e.g., sentences) in the source documents. Using an unsupervised learning technique (e.g., an automated and computerized technique without human intervention), the computing system can determine, based on learned word embeddings, an entry in the knowledge base that describes a concept that best represents an identified entity in a particular sequence of raw and unstructured text (e.g., a sentence) in a source document. The computing system can make such a determination for all the different sequences of raw and unstructured text in the source documents without any human intervention.

As mentioned above, the computing system may use any number of different methods for identifying entities in sequences of raw and unstructured text in the source documents. In one such method, the computing system recognizes entities in a sequence of raw and unstructured text based on learned word embeddings. Using another unsupervised learning technique (e.g., an automated and computerized technique without human intervention), the computing system employs a dynamically expanding window of words while comparing word embeddings for words in a sequence of raw and unstructured text with word embeddings for entries the knowledge base in order to identify entities in the sequence of raw and unstructured text.

In some embodiments, the computing system uses character embeddings instead of word embeddings to process raw and unstructured text in the source documents. The computing system may learn a variety of different-length character embeddings (e.g., two-character character embeddings, three-character character embeddings, four-character character embeddings, etc.). In some cases, the computing system may detect an unknown word in a sequence of raw and unstructured text (e.g., a learned word embedding does not exist for the word). In some such cases, the computing system can use the learned character embeddings to determine a word embedding for the unknown word. Once the unknown word has a word embedding, the computing system can perform word embedding operations on the unknown word, such as the aforementioned determination of an entry in the knowledge base that best represents an entity in the sequence of raw and unstructured text and identification of entities in the sequence of raw and unstructured text.

The technique described above for identifying entities in raw and unstructured text can be limiting in that it identifies a set number of different types of entities. In some embodiments, the computing system addresses this limitation by providing a technique for creating custom-defined tags that can be used to identify custom entity types in sequences of raw and unstructured text. To create a custom tag, the computing system receives several samples of sequences of words that are annotated as constituting the custom entity type. The computing system then defines a region in the vector space of the word embeddings based on the word embeddings for the sequences of words. Now, when the computing system processes sequences of raw and unstructured text, the computing system can determine words having word embeddings that fall within the defined region in the vector space as being a custom entity.

While the examples and embodiments described below are directed to medical data, one of ordinary skill in the art will understand that the techniques described herein are applicable to any discipline that has a specialized and/or relatively narrow vocabulary. For instance, these techniques can be applicable to the oil and gas industry, particular branches of engineering, finance, certain fields of law, etc. Furthermore, the techniques described here are also application to different languages. The English language is being used for examples and embodiments described below. However, if a similar corpus of medical data (or any corpus of data with a specialized and/or relatively narrow vocabulary) in a particular language is used to train embeddings (e.g., word embeddings, character embeddings, etc.), these techniques are equally applicable to the particular language.

The techniques described in the present application provide a number of benefits and advantages over conventional methods for processing raw and unstructured data. First, the unsupervised aspect of some of the techniques eliminates the need for human intervention, which is required in conventional methods for labeling and annotating data used to train machine learning models. In this fashion, thousands and thousands of hours of human intervention spent labeling and annotating data are saved using these techniques. Additionally, the techniques described herein are able to transform, without human intervention, raw and unstructured information in a discipline (e.g., medicine) that is inherently not computable absent a lot of human intervention and human training, into a standardized format that is computable (e.g., machine-readable).

1. High-Level Architecture

FIG. 1 illustrates a computing system 100 that processes documents based on embeddings according to some embodiments. As shown, computing system 100 includes word embedding manager 105, terminology manager 110, entity recognizer 115, unknown word manager 120, custom tags manager 125, and storages 130-145. Medical corpus data storage 130 is configured to store a corpus of medical data. Examples of such data include medical journals; academic journals related to medicine, nursing, pharmacy, dentistry, veterinary medicine, health care, etc.; clinical notes; etc. Medical corpus data storage 130 can also store pretrained vectors. Knowledge base storage 135 may store concepts and relationships among the concepts. In some embodiments, knowledge base storage 135 stores a medical terminology knowledge base that includes terminology entries. Knowledge base storage 135 can include terminology entries from a number of different terminology sources. Examples of such sources include SNOMED Clinical Terms (CT), RxNorm, Logical Observation Identifiers Names and Codes (LOINC), Current Procedural Terminology (CPT), International Classification of Diseases, Tenth Revision, Clinical Modification (ICD-10-CM), etc. Each terminology entry includes a text description of a concept and a unique identifier associated with the concept. In some such embodiments, embeddings determined for the entries are also stored in knowledge base storage 135.

Machine learning (ML) models storage 140 is configured to store ML models (e.g., neural networks). Examples of such ML models include an ML model for learning and determining word embeddings, an ML model for learning weights used for calculating confidence scores, different ML models for learning and determining different-length character embeddings, etc. ML models storage 140 may also store defined regions in embedding vector spaces. In some embodiments, ML models storage 140 stores third-party word embeddings. As shown in FIG. 1, computing system 100 receives source documents 150. Upon receiving them, computing system 100 stores them in source documents storage 145. In some embodiments, computing system 100 performs various preprocessing operations on source documents 150 before computing system 100 processes source documents 150 using the techniques described herein. Examples of such preprocessing operations include optical character recognition operations, computer vision operations, sectionalization operations, etc., described in U.S. patent application Ser. No. 16/432,592, filed Jun. 5, 2019. U.S. patent application Ser. No. 16/432,592 is incorporated herein by reference in its entirety for all purposes. Source documents 150 may include raw and unstructured information (e.g., text). For example, source documents 150 may be patient health records.

In some embodiments, storages 130-145 are implemented in a single physical storage while, in other embodiments, storages 130-145 may be implemented across several physical storages. While FIG. 1 shows storages 130-145 as part of computing system 100, one of ordinary skill in the art will appreciate that medical corpus data storage 130, knowledge base storage 135, ML models storage 140, and/or source documents storage 145 may be external to computing system 100 in some embodiments.

Word embedding manager 105 is responsible for generating word embeddings. In some embodiments, a word embedding is a vector representation of a word in a vector space. A vector representation of a word can have a defined number of dimensions (e.g., 200 dimensions, 250 dimensions, 300 dimensions, etc.). To produce word embeddings, word embedding manager 105 generates an ML model (e.g., a neural network) that includes word embeddings. Next, word embedding manager 105 initializes the values of the word embeddings in the ML model to a random set of values. Word embedding manager 105 then uses the medical data stored in medical corpus data storage 130 to train the word embeddings in the ML model. In some embodiments, word embedding manager 105 uses a skip-gram technique to train the ML model. Other techniques to train the ML model are possible. Word embedding manager 105 trains the ML model until a defined threshold convergence is reached. Once word embedding manager 105 finishes training the word embeddings in the ML model, a learned word embedding exists for each word in the medical data used to train the ML model. In some embodiments, a word embedding for a word may be determined by accessing the ML model and retrieving the word embedding. In other embodiments, word embedding manager 105 stores the learned word embeddings in a storage (not shown). In some such other embodiments, a word embedding for a word may be determined by accessing the storage and retrieving the word embedding.

Word embedding manager 105 also handles the generation of embeddings for entries in knowledge base storage 135. As mentioned above, in some embodiments, knowledge base storage 135 stores a medical terminology knowledge base that includes terminology entries where each terminology entry includes a text description of a concept and a unique identifier associated with the concept. Word embedding manager 105 may generate an embedding for a medical terminology entry by determining a word embedding for each word in the text description of the entry and calculating an average of the determined word embeddings for the words in the text description of the entry (i.e., adding the word embeddings together and dividing the sum by the total number of word embeddings). The calculated average is the embedding for the entry, which word embedding manager 105 stores in knowledge base storage 135. Word embedding manager 105 determines a word embedding for a particular word in the text description of an entry by retrieving the word embedding for the particular word from the ML model used to train the word embeddings or the storage used to store the learned word embeddings. In some instances, a learned word embedding may not exist for a particular word in the text description of an entry. In some such instances, word embedding manager 105 sends unknown word manager 120 a request for a word embedding for the particular word. Upon receiving the word embedding for the particular word from unknown word manager 120, word embedding manager 105 can calculate the average of the word embeddings for the words in the text description of the entry.

Terminology manager 110 is configured to determine the best entries in knowledge base storage 135 for sequences of raw and unstructured text in source documents 150. Terminology manager 110 makes such determinations after entities have been recognized (e.g., by entity recognizer 115 and/or other third-party entity recognizers) in the sequences of raw and unstructured text in source documents 150. For a particular sequence of raw and unstructured text in a source document 150, one or more sets of words may be recognized as an entity and determined to be one of a defined number of types of entities. In raw and unstructured medical documents (e.g., patient health records), the different types of entities may include a medication entity, a lab entity, a diagnosis entity, a procedure entity, and a vital entity. For each entity in a sequence of raw and unstructured text, terminology manager 110 determines an entry in the knowledge base that includes a textual description describing a concept that best represents the entity.

Entity recognizer 115 is responsible for recognizing entities in sequences of raw and unstructured text in source documents 150. In some embodiments, entity recognizer 115 employs several different techniques for recognizing entities in a sequence of raw and unstructured text. Entity recognizer 115 may also utilize third-party entity recognizers. Regardless of which techniques and/or third-party entity recognizes are used, entity recognizer 115 consolidates the entities identified from the various techniques and/or third-party entity recognizers. If there are any conflicting entities (the same word is identified as being different types of entities), entity recognizer 115 selects one of the entities as being the correct identified entity.

Unknown word manager 120 is configured to determine word embeddings for unknown words. In some embodiments, an unknown word is a word that does not have a learned word embedding. That is, an unknown word is a word that is not included in the corpus of data that word embedding manager 105 used to train word embeddings. When unknown word manager 120 receives a request to determine a word embedding for an unknown word, unknown word manager 120 uses character embeddings to determine a word, which has a word embedding, that is most similar to the unknown word. Once unknown word manager 120 determines the word that is most similar to the unknown word, unknown word manager 120 uses the word embedding for the determined word as the word embedding for the unknown word.

Custom tags manager 125 is responsible for managing custom-defined tags that are used to identify custom entity types. In some embodiments, custom tags manager 125 creates a custom tag using a number of different samples of sequences of words that are labeled as representing the same type of custom entity to define a region in the vector space for the word embeddings. Any type of custom tag may be created. For instance, custom tags can be created for identifying entities that are more generic than the types of entities recognized by entity recognizer 115. Custom tags may be created for identifying entities that are more specific than the types of entities recognized by entity recognizer 115. Once custom tags are created, custom tags manager 125 may use them to identify custom entity types in sequences of raw and unstructured text in source documents 150 based on word embeddings for the sequences of raw and unstructured text and the defined regions in the word embedding vector space.

2. Terminology Manager

Figure 2:
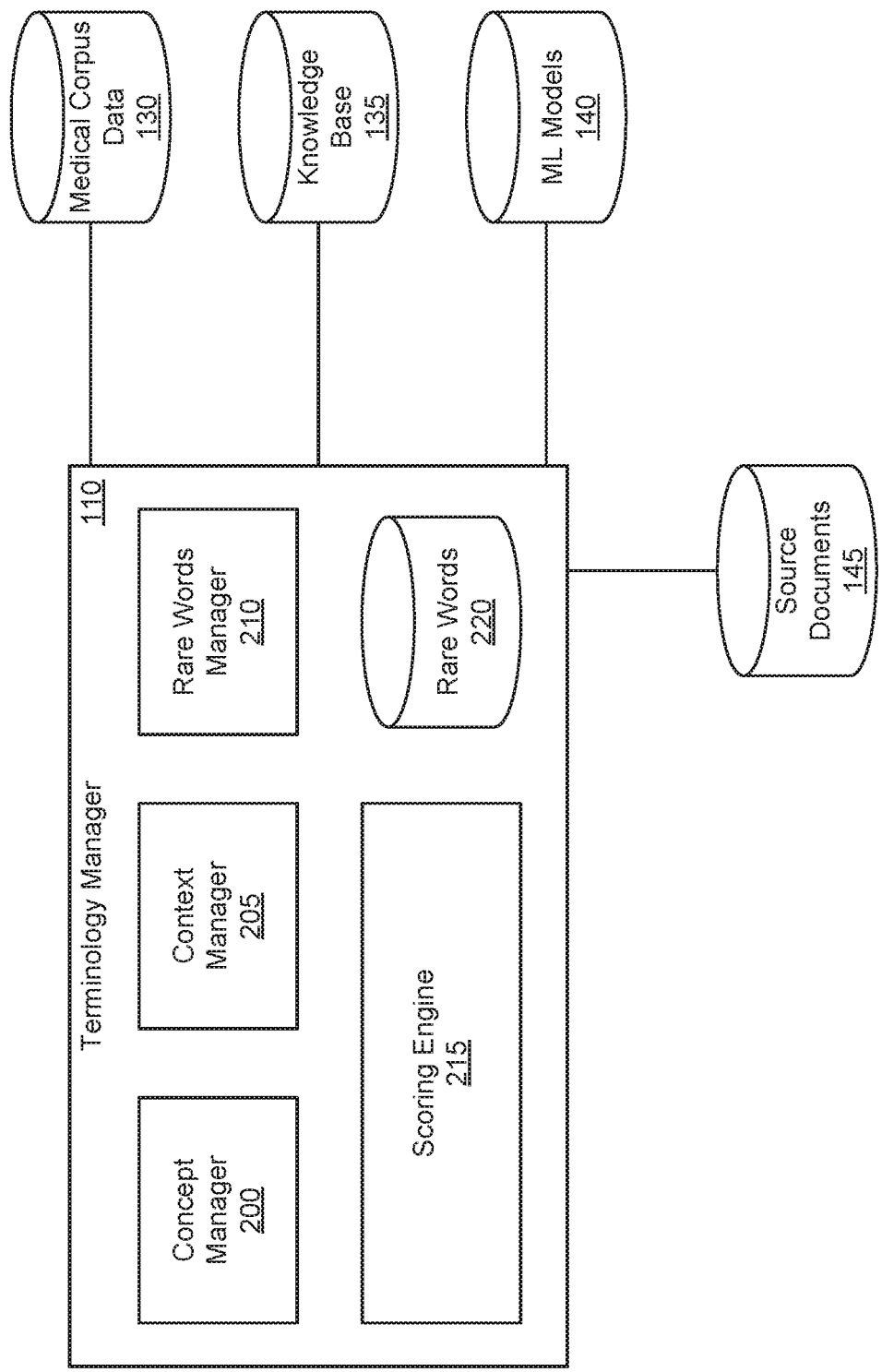
FIG. 2 illustrates an architecture of the terminology manager illustrated in FIG. 1 according to some embodiments.

FIG. 2 illustrates an architecture of terminology manager 110 according to some embodiments. As explained above, terminology manager 110 is configured to determine the best entries in knowledge base storage 135 for sequences of raw and unstructured text in source documents 150. As shown, terminology manager 110 includes concept manager 200, context manager 205, rare words manager 210, scoring engine 215, and rare words storage 220. Rare words storage 220 stores words that are determined to be rare words.

Concept manager 200 determines entries in knowledge base storage 135 for each entity a sequence of raw and unstructured text in a source document 150 based on concept. For example, when terminology manager 110 starts to process a sequence of raw and unstructured text from a source document 150 stored in source documents storage 145, concept manager 200 identifies a recognized entity in the sequence of raw and unstructured text. In some embodiments, a recognized entity represents a concept. Next, concept manager 200 determines a word embedding for the entity by accessing ML models storage 140 and retrieving it from the ML model used to train the word embeddings or the storage used to store the learned word embeddings. If a word embedding does not exist for the entity, concept manager 200 sends unknown word manager 120 a request for a word embedding for the entity. In return, concept manager 200 receives the word embedding for the entity from unknown word manager 120.

Concept manager 200 then accesses knowledge base storage 135 and retrieves all the entries in knowledge base storage 135 and their corresponding embeddings. Next, concept manager 200 calculates a vector distance between the embedding for the entity and each of the embeddings for the entries. In some embodiments, concept manager 200 calculates a vector distance between two embeddings by calculating a cosine similarity between the two embeddings. The value of a cosine similarity between two embeddings can be within the range of −1 and 1 where a cosine similarity value of 1 indicates that the embeddings have the same orientation and, thus, are close together while a cosine similarity value of −1 indicates that embeddings are diametrically opposed and, thus, are far apart. In other embodiments, concept manager 200 calculates a vector distance between two embeddings by calculating a Euclidean distance between the two embeddings.

Once the vector distances are calculated, concept manager 200 determines a list of a defined number (e.g., 50, 100, 200, etc.) of entries with embeddings that are closest to the embedding for the entity. That is, concept manager 200 determines a list of the defined number of the closest neighbors to the embedding for the entity in the word embedding vector space. Concept manager 200 then calculates concept scores for the list of entries based on the calculated vector distances. To calculate concept scores, concept manager 200 normalizes the calculated vector distance values for the list of entries to be between 0 and 1. For example, in some embodiments where cosine similarity is used as the vector distance, the possible cosine similarity values are between −1 and 1. In some such embodiments, concept manager 200 normalizes the similarity values by mapping them from a range of −1 and 1 to a range of 0 and 1. The normalized values are used as the concept scores for the entries in the list of entries.

In some embodiments, terminology manager 110 may determine the best entry for an entity based only on concept. In some such embodiments, terminology manager 110 determines the entry with the highest concept score in the list of entries as the entry in knowledge base storage 135 that describes a concept that best represents the entity and stores in source documents storage 145 an association between the entity in the sequence of raw and unstructured text and the determined best entry. In other embodiments, concept manager 200 sends the entity, the sequence of raw and unstructured text, the list of entries, and the concept scores for the entries to context manager 205 for further processing.

Concept manager 200 repeats the process described above for each recognized entity in the sequence of raw and unstructured text. Moreover, concept manager 200 processes each sequence of raw and unstructured text in the source documents 150 stored in source documents storage 145 in the same and/or similar manner.

Figure 3A:
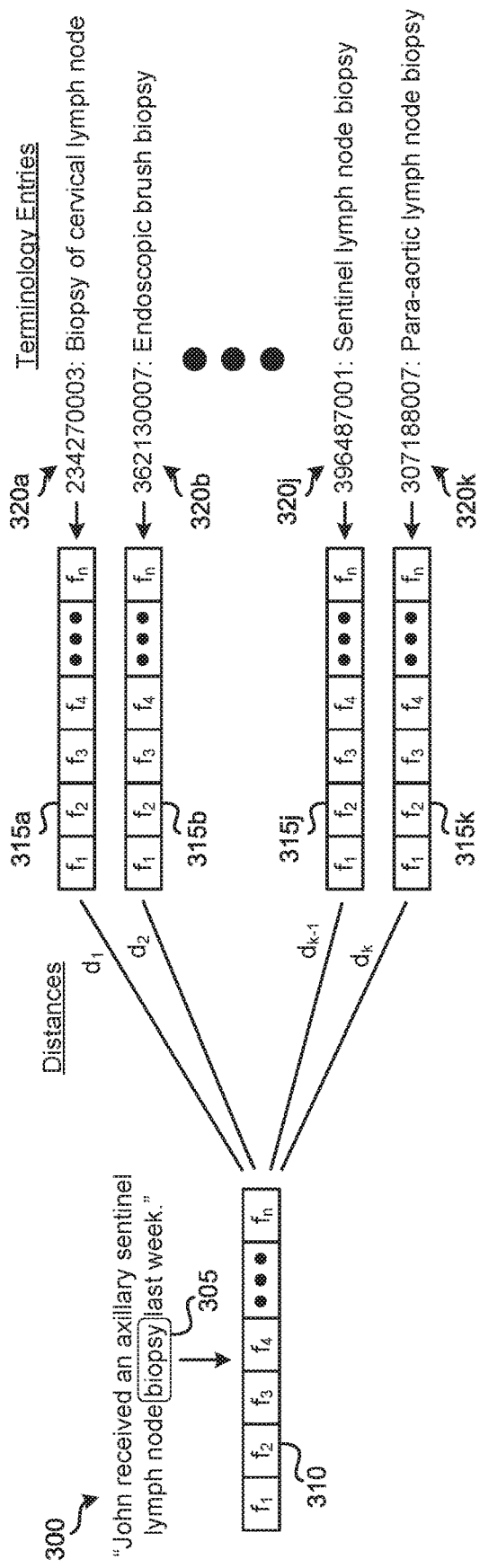
FIGS. 3A and 3B illustrate an example of determining a terminology entry for an entity according to some embodiments.
Figure 3B:
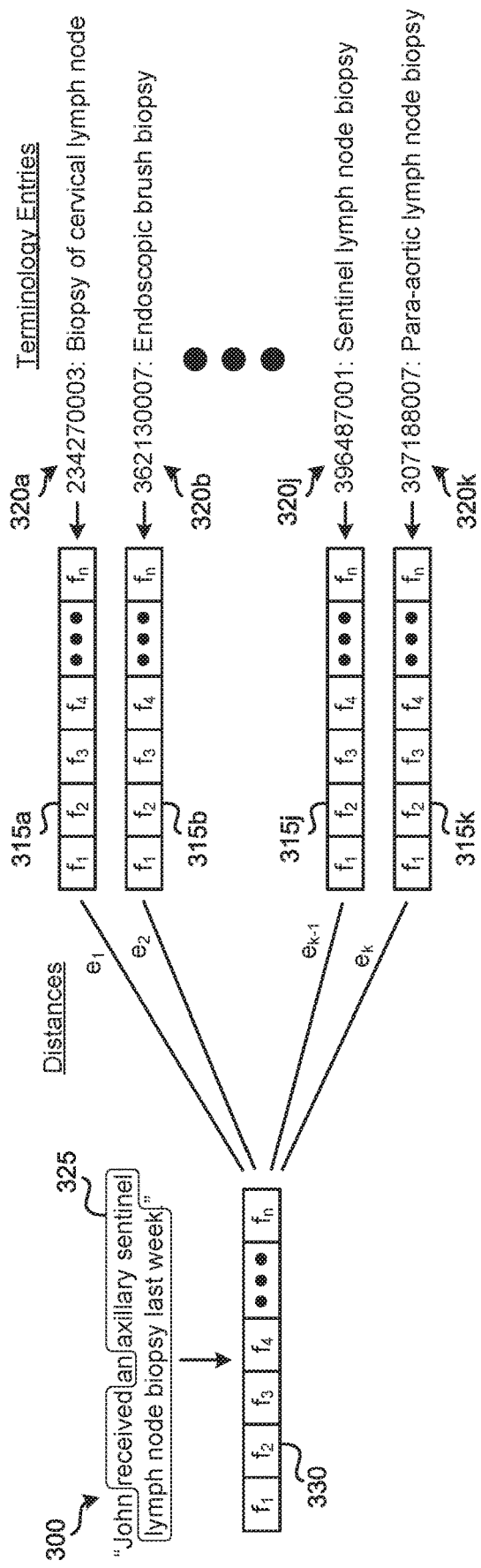

FIGS. 3A and 3B illustrate an example of determining a terminology entry for raw and unstructured text according to some embodiments. Specifically, FIG. 3A illustrates an example of determining medical terminology entries for an entity based on concept. FIG. 3A shows a sequence of raw and unstructured text 300 that includes a word ("biopsy" in this example) that has been recognized (e.g., by entity recognizer 115) as an entity 305. In this example, text 300 is a sentence in a source document 150 stored in source documents storage 145. As illustrated, concept manager 200 has determined word embedding 310 for entity 305 by accessing ML models storage 140 and retrieving it from the ML model used to train the word embeddings or the storage used to store the learned word embeddings. Word embedding 310 includes is an n-dimensional vector that includes n floating point values (i.e., real numbers). In this example, word embedding 310 represents the word "biopsy" in a vector space for the word embeddings.

FIG. 3A also illustrates medical terminology entries 320$a$-$k$ and embeddings 315$a$-315$k$ (which were determined by word embedding manager 105 as described above) that concept manager 200 retrieved from knowledge base storage 135. As shown, each terminology entry 320 includes a text description of a concept and a unique identifier associated with the concept. FIG. 3A further illustrates that each terminology entry 320 has an associated embedding 315. In this example, concept manager 200 calculates vector distances (e.g., cosine similarities) $d_1$-$d_k$ between the word embedding 310 for entity 305 and each of the embeddings 315$a$-315$k$ for the medical terminology entries 320$a$-$k$. After calculating vector distances $d_1$-$d_k$, for this example, concept manager 200 determined a list (not shown) of one hundred medical terminology entries 320 with embeddings that are closest to the embedding for entity 305 (i.e., medical terminology entries 320 associated with the shortest one hundred vector distances). Concept manager 200 may calculate concept scores for the medical terminology entries 320 in the list of medical terminology entries by normalizing the calculated vector distance values to fall within a range of 0 to 1 and using the normalized values as the concept scores for the medical terminology entries 320.

In some embodiments where terminology manager 110 determines the best medical terminology entry for an entity based only on concept, terminology manager 110 determines the medical terminology entry 320 with the highest concept score in the list of medical terminology entries as the medical terminology entry in knowledge base storage 135 that describes a concept that best represents entity 305. Terminology manager 110 then stores in source documents storage 145 an association between entity 305 and the determined best medical terminology entry 320. In other embodiments, concept manager 200 sends entity 305, text 300, the list of medical terminology entries, and the concept scores for medical terminology entries 320 to context manager 205 for further processing.

Returning to FIG. 2, context manager 205 is configured to determine the best entry in knowledge base storage 135 for each entity a sequence of raw and unstructured text in a source document 150 based on concept and context. Upon receiving from concept manager 200 an entity, a sequence of raw and unstructured text, a list of entries, and concept scores for the entries, context manager 205 determines a subset of words in the sequence of raw and unstructured text based on a defined size window of words. In some embodiments, context manager 205 determines the subset of words in the sequence of raw and unstructured text to include the entity, a defined number (e.g., two, three, five, etc.) of words before the entity, and a defined number (e.g., two, three, five, etc.) of words after the entity. In some such embodiments, context manager 205 does not include words in the sequence of raw and unstructured text that are in a list of defined stop words (e.g., "the", "a", "an", "of", etc.). In some embodiments, an entity in such a subset of words represents a concept and the remaining words in the subset of words represent a context associated with the entity. As such, the subset of words collectively represents a concept and its context.

After determining the subset of words, context manager 205 generates an embedding for the subset of words. In some embodiments, context manager 205 does so by determining a word embedding for each word in the subset of words and calculating an average of the determined word embeddings for the subset of words (i.e., adding the word embeddings together and dividing the sum by the total number of word embeddings). The calculated average is the embedding generated for the subset of words. Context manager 205 may determine a word embedding for a particular word in the subset of words by retrieving the word embedding for the particular word from the ML model used to train the word embeddings or the storage used to store the learned word embeddings. In some cases, a learned word embedding does not exist for a particular word in the subset of words. In some such cases, context manager 205 sends unknown word manager 120 a request for a word embedding for the particular word. Once context manager 205 receives the word embedding for the particular word from unknown word manager 120, context manager 205 may calculate the average of the word embeddings for the subset of words.

Next, context manager 205 calculates a vector distance between the embedding generated for the subset of words and each of the embeddings for the entries in the list of entries. Context manager 205 can calculate a vector distance between two embeddings by calculating a cosine similarity between the two embeddings in some embodiments. As explained above, the value of a cosine similarity between two embeddings can be within the range of −1 and 1 where a cosine similarity value of 1 indicates that the embeddings have the same orientation and, thus, are close together while a cosine similarity value of −1 indicates that embeddings are diametrically opposed and, thus, are far apart. In other embodiments, context manager 205 may calculate a vector distance between two embeddings by calculating a Euclidean distance between the two embeddings.

After context manager 205 calculates the vector distances, context manager 205 calculates context scores for the list of entries based on the calculated vector distances. In some embodiments, context manager 205 calculates context scores by normalizing the calculated vector distance values for the entries in the list of entries to be between 0 and 1. For instance, in some embodiments where cosine similarity is used as the vector distance, the possible cosine similarity values are between −1 and 1. As such, in some such embodiments, context manager 205 normalizes the similarity values by mapping them from a range of −1 and 1 to a range of 0 and 1. The normalized values are used as the context scores for the entries in the list of entries.

In some embodiments where terminology manager 110 determines the best entry for an entity based only on concept and context, terminology manager 110 determines the entry with the highest context score in the list of entries as the entry in knowledge base storage 135 that describes a concept that best represents the entity and stores in source documents storage 145 an association between the entity in the sequence of raw and unstructured text and the determined entry. In other embodiments, context manager 205 sends the entity, the sequence of raw and unstructured text, the list of entries, the concept scores for the entries, and the context scores for the entries to rare words manager 210 for additional processing.

Returning to the example of determining a terminology entry for raw and unstructured text illustrated in FIGS. 3A and 3B, FIG. 3B illustrates an example of determining a medical terminology entry 320 for entity 305 based on concept and context. In this example, context manager 205 receives from concept manager 200 entity 305, text 300, the list of medical terminology entries, and the concept scores for medical terminology entries 320. In response to receiving these data, context manager 205 determines a subset of words 325 in text 300 based on a defined size window of words. For this example, the size of the window of words is entity 305, five words before entity 305, and five words after entity 305. Context manager 205 does not include in the subset of words 325 the word "an" in text 300 because it is included in a list of defined stop words. Based on this defined window of words, context manager 205 determines the subset of words 325 in text 300.

Next, context manager 205 generates an embedding 330 for the subset of words 325 determining a word embedding for each word in the subset of words 325 and calculating an average of the determined word embeddings for the subset of words 325. The calculated average is embedding 330 generated for the subset of words 325. In this example, context manager 205 determined a word embedding for a particular word in the subset of words 325 by retrieving the word embedding for the particular word from the ML model used to train the word embeddings or the storage used to store the learned word embeddings. Context manager 205 then calculates vector distances (e.g., cosine similarities) $e_1$-$e_k$ between embedding 330 generated for the subset of words 325 and each of the embeddings 315 for medical terminology entries 320 in the list of medical terminology entries. Once context manager 205 finishes calculating the vector distances $e_1$-$e_k$, concept manager 200 calculates context scores for the medical terminology entries 320 in the list of medical terminology entries by normalizing the calculated vector distance values to fall within a range of 0 to 1 and using the normalized values as the context scores for the medical terminology entries 320 in the list of medical terminology entries.

In some embodiments where terminology manager 110 determines the best medical terminology entry for an entity based only on concept and context, terminology manager 110 determines the medical terminology entry 320 with the highest context score in the list of medical terminology entries as the medical terminology entry in knowledge base storage 135 that describes a concept that best represents entity 305. In some such embodiments, terminology manager 110 stores in source documents storage 145 an association between entity 305 and the determined best medical terminology entry 320. In other embodiments, context manager 205 sends entity 305, text 300, the list of medical terminology entries, the concept scores for medical terminology entries 320, and the context scores for medical terminology entries 320 to rare words manager 215 for further processing.

Rare words manager 210 is in charge of determining rare words. In some embodiments, rare words manager 210 determines rare words by accessing the medical data stored in medical corpus data storage 130 (i.e., the data word embedding manager 105 used to train word embeddings) and calculating a term frequency-inverse document frequency (TF-IDF) score for each unique word in a document in the medical data. In some such embodiments, for each unique word in the medical data, rare words manager 210 determines the highest TF-IDF score for the word and stores it in rare words storage 220 as the TF-IDF score for the word. In other such embodiments, for each unique word in the medical data, rare words manager 210 calculates a sum of all the TF-IDF scores for the word and stores it in rare words storage 220 as the TF-IDF score for the word.

Once rare words manager 210 has determined rare words, rare words manager 210 is able to determine rare word scores for the entries in the list of entries. For instance, when rare words manager 210 receives from context manager 205 an entity, a sequence of raw and unstructured text, a list of entries, concept scores for the entries, and context scores for the entries, rare words manager 210 calculates a rare word score for each entry in the list of entries. In some embodiments, rare words manager 210 calculates a rare word score for an entry in the list of entries by accessing rare words storage 220 and retrieving the TF-IDF score for each word in the sequence of raw and unstructured text in order to determine a sequence of TF-IDF scores for the sequence of raw and unstructured text. Next, rare words manager 210 identifies words in the sequence of raw and unstructured text that also occur in the text description of the entry and calculates a sum of the TF-IDF scores of the identified words. in some embodiments, rare works manager 210 identifies words in the sequence of raw and unstructured text that also occur in the text description of the entry by stemming the words in the sequence of raw and unstructured text, stemming the words in the text description of the entry, and comparing the stemmed words in the sequence of raw and unstructured text with the stemmed the words in the text description of the entry. After calculating TF-IDF scores for the entries in the list of entries, rare words manager 210 normalizes the determined number of common rare words to a range between 0 and 1. In some embodiments, rare words manager 210 normalizes the TF-IDF scores using the following equation:

$$score_{new} = \frac{score - score_{min}}{score_{max} - score_{min}}$$

where score is a calculated TF-IDF score for a particular entry in the list of entries, $score_{min}$ is the lowest calculated TF-IDF score for an entry in the list of entries, $score_{max}$ is the highest calculated TF-IDF score for an entry in the list of entries, and $score_{new}$ is the normalized TF-IDF score for the particular entry in the list of entries. The normalized TF-IDF score is the rare words score for the entry. Finally, rare words manager 210 sends the entity, the list of entries, concept scores for the entries, context scores for the entries, and rare words scores for the entries to scoring engine 215 for further processing.

Scoring engine 215 is configured to generate confidence scores for entries. For example, scoring engine 215 may receive from rare words manager 210 an entity, a list of entries, concept scores, context scores, and rare words scores, scoring engine 215 generates confidences scores for each entry in the list of entries. In some embodiments, scoring engine 215 generates a confidence score for an entry by calculating a weighted average of the concept score for the entry, the context score for the entry, and the rare words score for the entry. Scoring engine 215 may use the following equation to calculate a confidence score:

$$confidence = \frac{concept \times w_1 + context \times w_2 + rare\ words \times w_3}{w_1 + w_2 + w_3}$$

wherein confidence is a confidence score for an entry, concept is a concept score for the entry, context is a context score for the entry, rare words is a rare words score for the entry, and $w_1$ is a weight value for the concept score, $w_2$ is a weight value for the context score, and $w_3$ is a weight value for the rare words score. In some embodiments, scoring engine 215 uses the same weight value for the concept score, the context score, and the rare words score. In other embodiments, scoring engine 215 uses custom-defined weight values for the concept score, the context score, and the rare words score. In yet other embodiments, scoring engine 215 uses weight values for the concept score, the context score, and the rare words score that are learned using an ML model (e.g., a neural network). In some embodiments where terminology manager 110 determines the best medical terminology entry for an entity based only on concept, context, and rare words, terminology manager 110 determines the entry with the highest calculated confidence score as the entry that describes a concept that best represents the entity.

To determine weight values learned from an ML model, scoring engine 215 first receives several mappings (e.g., associations) determined by terminology manager 110 that correctly maps an entity in a sequence of raw and unstructured text in source documents 150 to an entry in knowledge base storage 135 describing a concept that best represents the entity. These mappings are reviewed by a user and confirmed as being correct. Therefore, the several mappings do not include any mappings determined by terminology manager 110 that incorrectly maps an entity in a sequence of raw and unstructured text in source documents 150 to an entry in knowledge base storage 135 (i.e., the entry describes a concept that does not best represent the entity).

Figure 4:
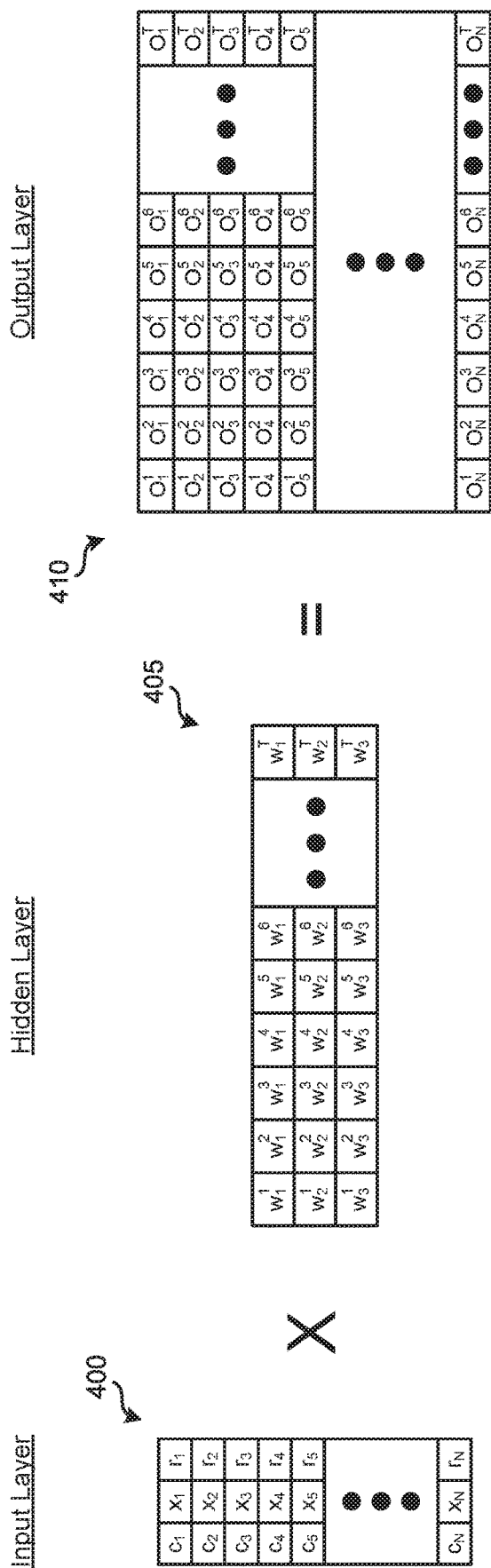
FIG. 4 illustrates an example of determining weights for calculating confidence scores according to some embodiments.

Next, scoring engine 215 generates an ML model for learning the weight values for the concept score, context score, and rare words score. FIG. 4 illustrates an example of determining weights for calculating confidence scores according to some embodiments. Specifically, FIG. 4 illustrates example matrices used in a neural network for learning weights for calculating confidence scores. For this example, scoring engine 215 received N number of mappings determined by terminology manager 110 that correctly maps an entity in a sequence of raw and unstructured text in source documents 150 to an entry in knowledge base storage 135 describing a concept that best represents the entity. In addition, there are T number of total entries stored in knowledge base storage 135.

As shown, an input layer of the neural network includes a is N×3 matrix 400. Each row in matrix 400 stores a concept score $c_i$, a context score $x_i$, and a rare words score $r_i$ calculated for an entry in one of the received mappings. In addition, FIG. 4 shows a hidden layer that includes a 3×T matrix 405. Each row in matrix 405 includes a score weight for each of the T entries. In particular, the first row of matrix 405 includes a concept score weight for each of the T entries, the second row of matrix 405 includes a context score weight for each of the T entries, and the third row of matrix 405 includes a rare words score weight for each of the T entries. Lastly, FIG. 4 illustrates an N×T matrix 410. Each row in matrix 410 stores an output that predicts an entry for a corresponding entity in the input layer. The output of a row includes output values for each of the T entries where the highest output value in the row is the predicted entry for the corresponding entity.

In this example, a softmax distribution function is applied to the dot product of matrix 400 and matrix 405. As a result, the T number of output values in each row of matrix 410 is transformed from floating numbers to a probability distribution where the output values fall within a range of 0 to 1 and the sum of the output values equals 1. Hence, the output values in the first row of matrix 410 add up to 1, the output values in the second row of matrix 410 add up to 1, the output values in the third row of matrix 410 add up to 1, etc. To train the neutral network represented by matrices 400-410, scoring engine 215 uses any number of different ML techniques to adjust the weight values in matrix 405 so that the correct entry in matrix 410 is predicted for the corresponding entity in matrix 400.

After scoring engine 215 finishes training the neural network and, thus, the weights in matrix 405 are learned, scoring engine 215 calculates an average value of the weight values in each row of matrix 405. The average of the weight values in the first row of matrix 405 is the learned weight value for the concept score, the average of the weight values in the second row of matrix 405 is the learned weight value for the context score, and the average of the weight values in the third row of matrix 405 is the learned weight value for the rare words score.

Figure 5:
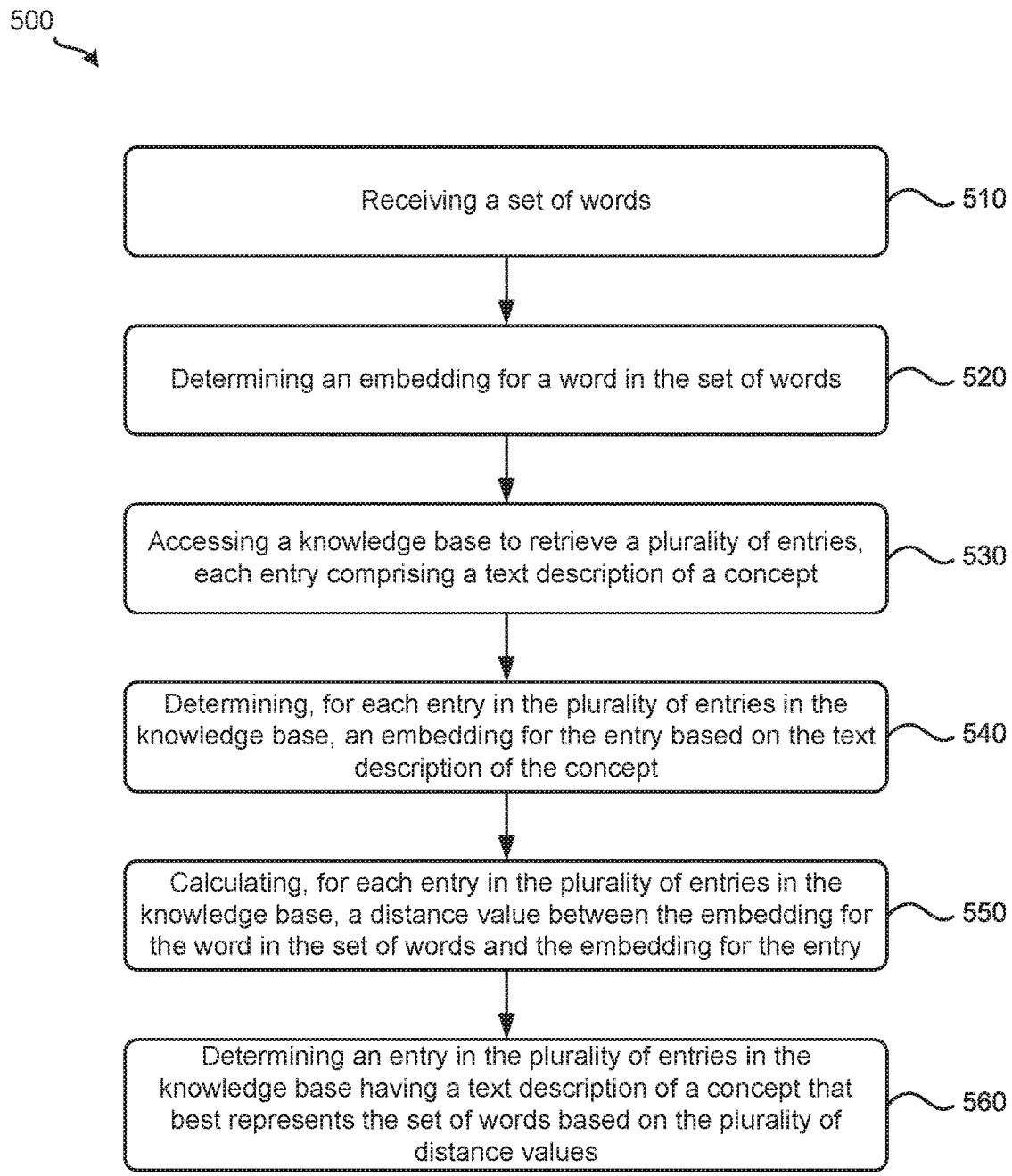
FIG. 5 illustrates a process for determining an entry in a knowledge base for an entity according to some embodiments.

FIG. 5 illustrates a process 500 for determining an entry in a knowledge base for an entity according to some embodiments. In some embodiments, computing system 100 performs process 500. Process 500 starts by receiving, at 510 a set of words. Referring to FIGS. 2 and 3 as an example, concept manager 200 can receive a sequence of raw and unstructured text 300 in a source document 150 from source documents storage 145.

Next, process 500 determines, at 520, an embedding for a word in the set of words. Referring to FIGS. 2 and 3 as an example, text 300 includes a word "biopsy" that has been recognized as entity 305. Concept manager 200 determined word embedding 310 for entity 305 by accessing ML models storage 140 and retrieving it from the ML model used to train the word embeddings or the storage used to store the learned word embeddings. After operation 520, process 500 accesses, at 530, a knowledge base to retrieve a plurality of entries. Each entry comprising a text description of a concept. Referring to FIGS. 2 and 3 as an example, concept manager 200 accesses knowledge base storage 135 to retrieve medical terminology entries 320a-k and embeddings 315a-315k.

Process 500 then determines, at 540, for each entry in the plurality of entries in the knowledge base, an embedding for the entry based on the text description of the concept. Referring to FIGS. 1 and 3 as an example, word embedding manager 105 generated embeddings for medical terminology entries 320a-k. For each of the medical terminology entries 320a-k, word embedding manager 105 determined a word embedding for each word in the text description of the medical terminology entry 320 and calculated an average of the determined word embeddings for the words in the text description of the medical terminology entry 320.

Next, process 500 calculates, at 550, for each entry in the plurality of entries in the knowledge base, a distance value between the embedding for the word in the set of words and the embedding for the entry. Referring to FIGS. 2 and 3 as an example, concept manager 200 calculates vector distance values $d_1$-$d_k$ for medical terminology entries 320a-k by calculating cosine similarities between word embedding 310 and embeddings 315a-k.

Finally, process 500 determines, at 560, an entry in the plurality of entries in the knowledge base having a text description of a concept that best represents the set of words based on the plurality of distance values. Referring to FIGS. 2 and 3 as an example, concept manager 200 determined a list of one hundred medical terminology entries 320 with embeddings that are closest to the embedding for entity 305 and calculates concept scores for medical terminology entries 320 in the list of medical terminology entries by normalizing the calculated vector distance values to fall within a range of 0 to 1 and using the normalized values as the concept scores for the medical terminology entries 320. Terminology manager 110 then determines the medical terminology entry 320 with the highest concept score in the list of medical terminology entries as the medical terminology entry in knowledge base storage 135 that describes a concept that best represents entity 305.

The examples and embodiments described above in this section illustrate the use of vector distances between embeddings to determine an entry that describes a concept that best represents an entity in a sequence of raw and unstructured text. In some embodiments, the resulting determinations may be used to perform supervised training on a ML model so that that, given an entity in a sequence of raw and unstructured text, the ML model can correctly predict an entry that describes a concept that best represents the entity. For instance, the determinations based on vector distances can be reviewed and checked for correctness. The correct determinations can be used as the input and output when training the ML model. Such an ML model can determine an entry that describes a concept that best represents an entity in a sequence of raw and unstructured text without relying on vector distances.

3. Entity Recognizer

Figure 6:
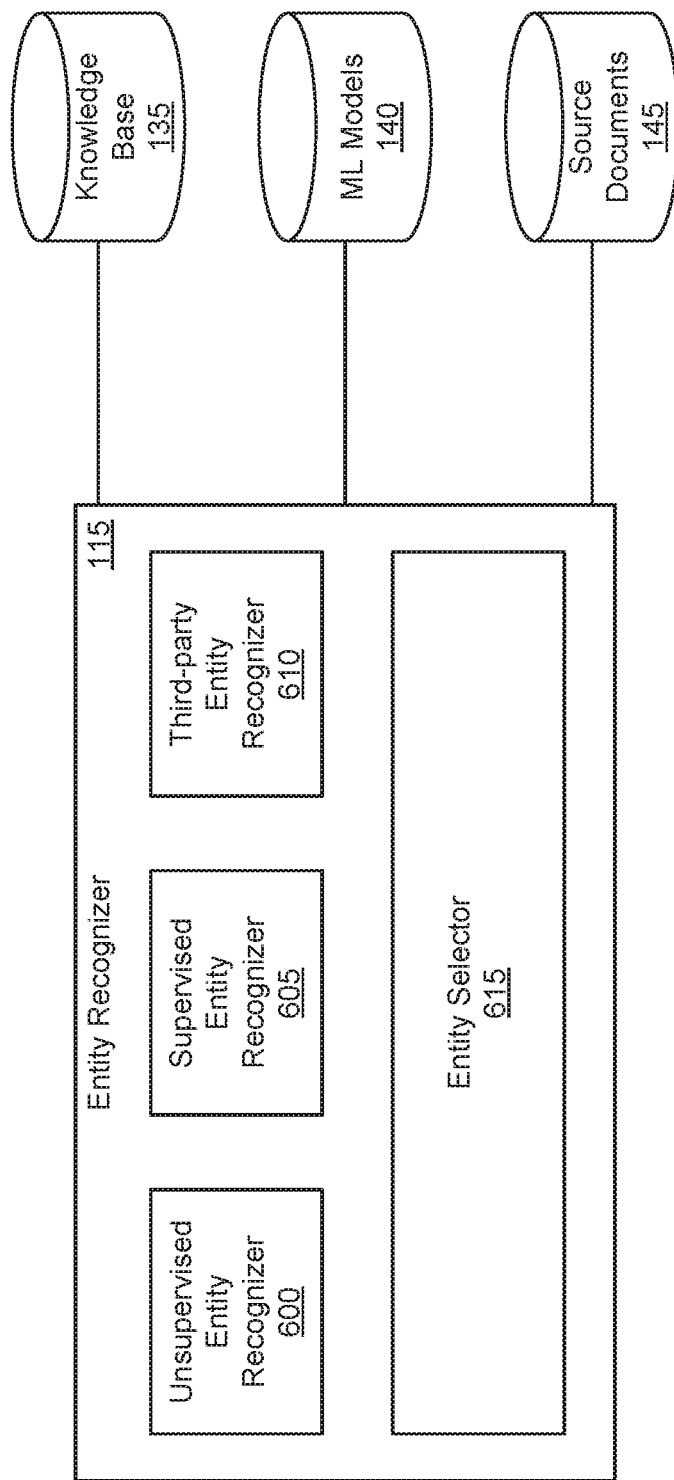
FIG. 6 illustrates an architecture of the entity recognizer illustrated in FIG. 1 according to some embodiments.

FIG. 6 illustrates an architecture of entity recognizer 115 illustrated in FIG. 1 according to some embodiments. As shown, entity recognizer 115 includes unsupervised entity recognizer 600, supervised entity recognizer 605, third-party entity recognizer 610, and entity selector 615. Third-party entity recognizer 610 may be a third-party tool configured to recognize entities in raw and unstructured text.

As described above, entity recognizer 115 recognizes entities in sequences of raw and unstructured text in source documents 150. Entity recognizer 115 processes source documents 150 stored in source documents storage 145 on a sequence of raw and unstructured text by sequence of raw and unstructured text basis. When processing a particular sequence of raw and unstructured text in a source document 150, entity recognizer 115 sends the particular sequence of raw and unstructured text to each of unsupervised entity recognizer 600, supervised entity recognizer 605, third-party entity recognizer 610. The entity (or entities) selected by entity selector 615 is the entity recognized in the particular sequence of raw and unstructured text. Entity recognizer 115 stores this information in source documents storage 145.

Unsupervised entity recognizer 600 is configured to recognize entities in sequences of raw and unstructured text based on learned word embeddings. For example, upon receiving a sequence of raw and unstructured text, unsupervised entity recognizer 600 removes words in the sequence of raw and unstructured text that are included in a list of defined stop words. Next, unsupervised entity recognizer 600 retrieves an entry and an embedding associated with the entry from knowledge base storage 135. Starting with a default size of 1 for a window of words, unsupervised entity recognizer 600 identifies a word in the sequence of raw and unstructured text and determines a word embedding for the identified word (e.g., by retrieving the word embedding for each word in the window of words from the ML model used to train the word embeddings or the storage used to store the learned word embeddings and calculating an average of the determined word embeddings). Next, unsupervised entity recognizer 600 calculates a confidence score for the entry with respect to the identified word based on the embedding for the entry and the word embedding for words in the window of words. In some embodiments, unsupervised entity recognizer 600 calculates the confidence score using the same technique used by terminology manager 110 for calculating context scores as described above by reference to FIGS. 2, 3B, and 5. In other embodiments, unsupervised entity recognizer 600 sends terminology manager 110 the sequence of raw and unstructured text, the words in the window of words, and the entry along with a request to calculate a context score based on that data. In return, unsupervised entity recognizer 600 receives the confidence score from terminology manager 110.

If the confidence score for the entry with respect to the identified word is less than a defined threshold amount, unsupervised entity recognizer 600 resets the size of the window of words to the default value of 1, iterates to the next word in the sequence of raw and unstructured text, and calculates a confidence score for the next word in the same manner as that described above. If the confidence score for the entry with respect to the identified word is not less than (i.e., greater than or equal to) the defined threshold amount and is greater than or equal to a previous calculated confidence score (e.g., the confidence score calculated for the entry with respect to the previous word (that is not a stop word) in the sequence of raw and unstructured text), unsupervised entity recognizer 600 increases the windows size of the window of words by 1, iterates to the next word in the sequencer of raw and unstructured text, and calculates the confidence score for the next word in the same manner as that described above. If the confidence score for the entry with respect to the identified word is not less than (i.e., greater than or equal to) the defined threshold amount and is not greater than or equal to (i.e., less than) the previous calculated confidence score, unsupervised entity recognizer 600 determines that the previous window of words is an entity, resets the size of the window of words to the default value of 1, iterates to the next word in the sequencer of raw and unstructured text, and calculates the confidence score for the next word in the same manner as that described above. Unsupervised entity recognizer 600 continues processing words in the sequence of raw and unstructured text in the manner described above until no more words are left.

Figure 7A:
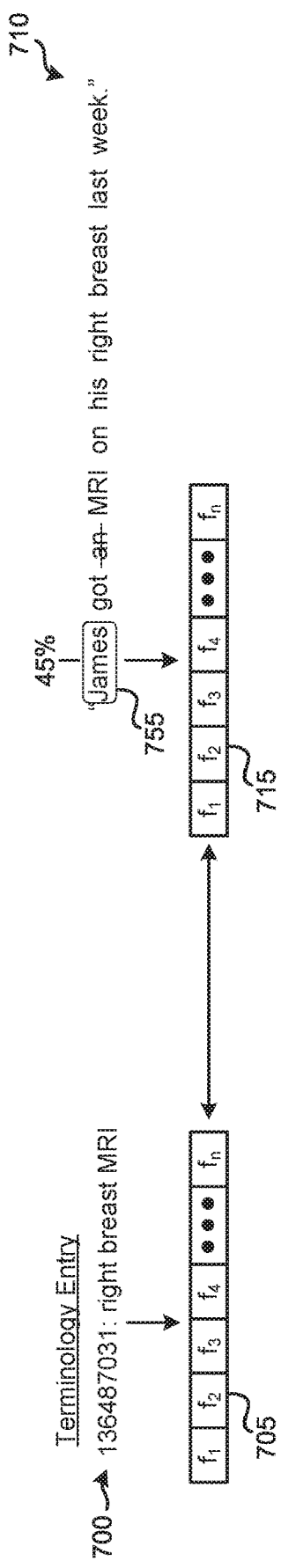

FIGS. 7A-7J illustrate an example of recognizing an entity in raw text according to some embodiments. Specifically, FIGS. 7A-7J illustrate an example of unsupervised entity recognizer 600 recognizing an entity in a sequence of raw and unstructured text 710 based on a medical terminology entry 700 stored in knowledge base storage 135. As shown in FIG. 7A, for this example, unsupervised entity recognizer 600 has retrieved medical terminology entry 700 and an embedding associated with medical terminology entry 700 (which was determined by word embedding manager 105 as described above) from knowledge base storage 135. Medical terminology entry 700 includes a text description of a concept and a unique identifier associated with the concept.

In this example, unsupervised entity recognizer 600 has received a sequence of raw and unstructured text 710 from a source document 150 stored in source documents storage 135. Unsupervised entity recognizer 600 has removed the word "an" from text 710, as indicated by a strikethrough of the word. FIG. 7A also illustrates that unsupervised entity recognizer 600 has identified a word ("James" in this example) in text 710. Additionally, unsupervised entity recognizer 600 has determined a word embedding 715 for the identified word by retrieving the word embedding for words in window of words 755 from the ML model used to train the word embeddings or the storage used to store the learned word embeddings. Unsupervised entity recognizer 600 has also initialized the size of a window of words 755 to a default size of 1 (i.e., 1 word). FIG. 7A also shows that unsupervised entity recognizer 600 has calculated a confidence score in the same manner described above for medical terminology entry 700 with respect to the identified word based on embedding 705 for medical terminology entry 700 and word embedding 715 for words in window of words 755. For this example, the calculated confidence score for the identified word (45% in this example) is less than a defined threshold score of 90%. Thus, unsupervised entity recognizer 600 resets the size of the window of words to the default value of 1, iterates to the next word in the sequence of raw and unstructured text, and calculates a confidence score for the next word.

Figure 7B:
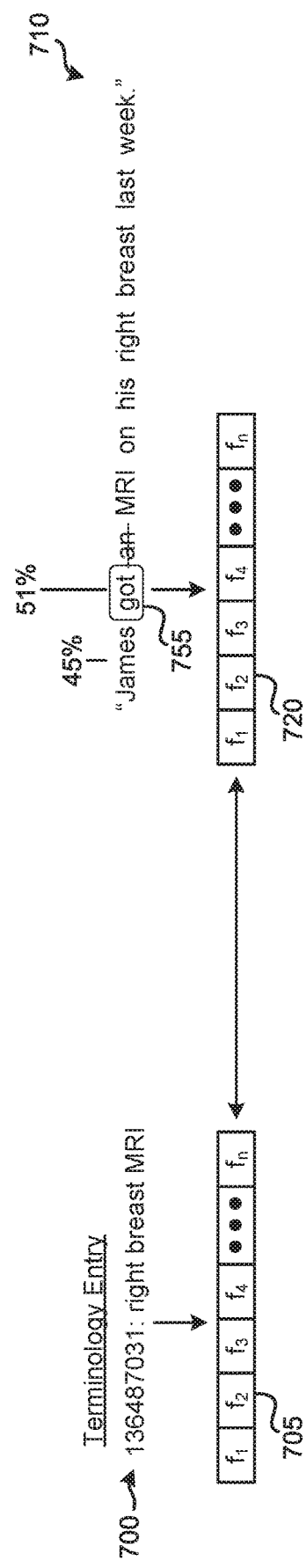

FIG. 7B illustrates the next stage in the example where unsupervised entity recognizer 600 has processed the next word in text 710. As shown, unsupervised entity recognizer 600 has identified the next word in text 710 ("got" in this example), reset the size of window of words 755 to the default size of 1, and calculated a confidence score for medical terminology entry 700 with respect to the identified word based on embedding 705 for medical terminology entry 700 and word embedding 720 for words in window of words 755. For this example, window of words 755 is a trailing window that ends at the current identified word. Since "got" is the current identified word and the size of window of words 755 is 1, window of words 755 includes the word "got". As shown in FIG. 7B, the calculated confidence score for the identified word (51% in this example) is less than the defined threshold score of 90%. Therefore, unsupervised entity recognizer 600 resets the size of the window of words to the default value of 1, iterates to the next word in the sequence of raw and unstructured text, and calculates a confidence score for the next word.

Figure 7C:
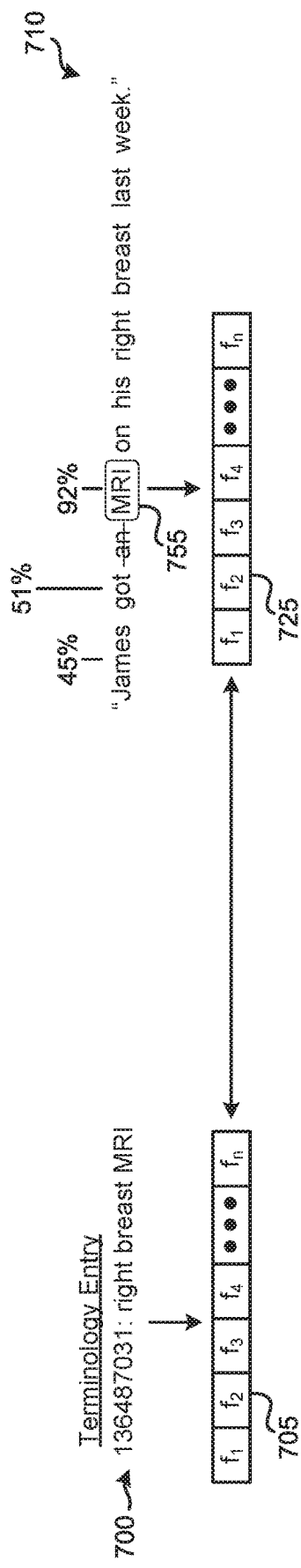

At the third stage in the example illustrated in FIG. 7C, unsupervised entity recognizer 600 has processed the next word in text 710. As shown, unsupervised entity recognizer 600 has identified the next word in text 710 ("MRI" in this example as the word "an" has been removed), reset the size of window of words 755 to the default size of 1, and calculated a confidence score for medical terminology entry 700 with respect to the identified word based on embedding 705 for medical terminology entry 700 and word embedding 725 for words in window of words 755. Because "MRI" is the current identified word and the size of window of words 755 is 1, window of words 755 includes the word "MRI". The calculated confidence score for the identified word (92% in this example) is not less than (i.e., greater than or equal to) the defined threshold score of 90% and is greater than or equal to the previous calculated confidence score (e.g., the confidence score calculated for the entry with respect to the word "got" in text 710), as illustrated in FIG. 7C. As such, unsupervised entity recognizer 600 increases the size of the window of words to the value of 2, iterates to the next word in the sequence of raw and unstructured text, and calculates a confidence score for the next word.

Figure 7D:
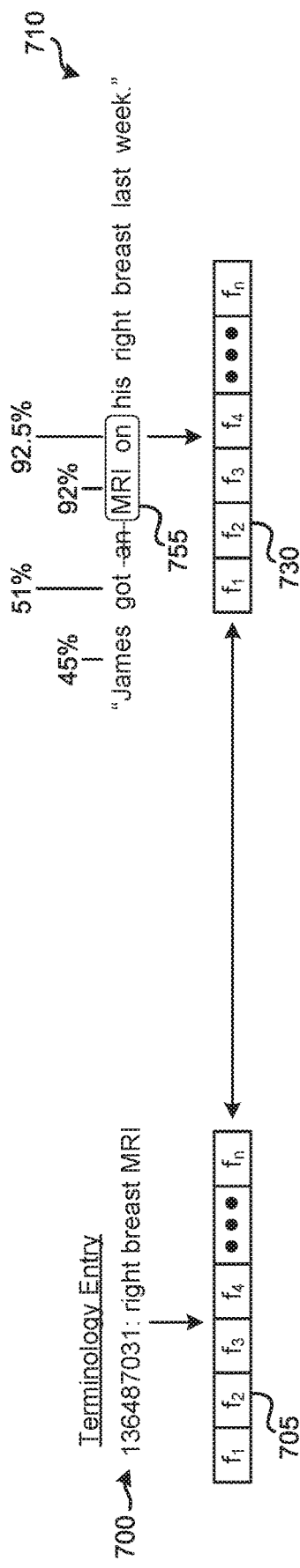

FIG. 7D illustrates the next stage in the example where unsupervised entity recognizer 600 has processed the next word in text 710. Unsupervised entity recognizer 600 has identified the next word in text 710 ("on" in this example), increased the size of window of words 755 to the size of 2, and calculated a confidence score for medical terminology entry 700 with respect to the identified word based on embedding 705 for medical terminology entry 700 and word embedding 730 for words in window of words 755 (e.g., an average of word embeddings of each of the words in window of words 755), as shown in FIG. 7D. As mentioned above, window of words 755 is a trailing window that ends at the current identified word. Since the current identified word is "on" and the size of window of words 755 is 2, window of words 755 includes the words "MRI on". Because the calculated confidence score for the identified word (92.5% in this example) is not less than (i.e., greater than or equal to) the defined threshold score of 90% and is greater than or equal to the previous calculated confidence score (e.g., the confidence score calculated for the entry with respect to the word "MRI" in text 710), unsupervised entity recognizer 600 increases the size of the window of words to the value of 3, iterates to the next word in the sequence of raw and unstructured text, and calculates a confidence score for the next word.

Figure 7E:
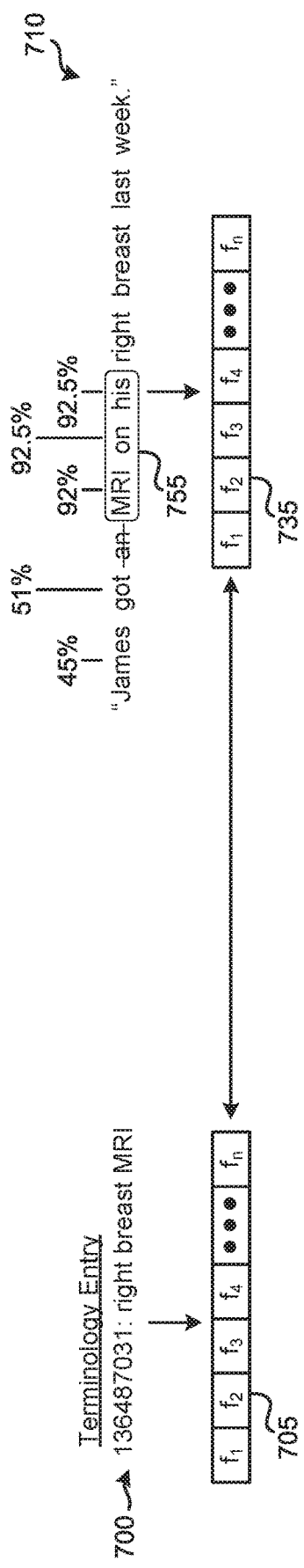

The fifth stage in the example shown in FIG. 7E, unsupervised entity recognizer 600 has processed the next word in text 710. As illustrated, unsupervised entity recognizer 600 has identified the next word in text 710 ("his" in this example), increased the size of window of words 755 to the size of 3, and calculated a confidence score for medical terminology entry 700 with respect to the identified word based on embedding 705 for medical terminology entry 700 and word embedding 735 for words in window of words 755 (e.g., an average of word embeddings of each of the words in window of words 755). Here, window of words 755 includes the words "MRI on his" as the current identified word is "his" and the size of window of words 755 is 3. The calculated confidence score for the identified word (92.5% in this example) is not less than (i.e., greater than or equal to) the defined threshold score of 90% and is greater than or equal to the previous calculated confidence score (e.g., the confidence score calculated for the entry with respect to the word "on" in text 710). Hence, unsupervised entity recognizer 600 increases the size of the window of words to the value of 4, iterates to the next word in the sequence of raw and unstructured text, and calculates a confidence score for the next word.

Figure 7F:
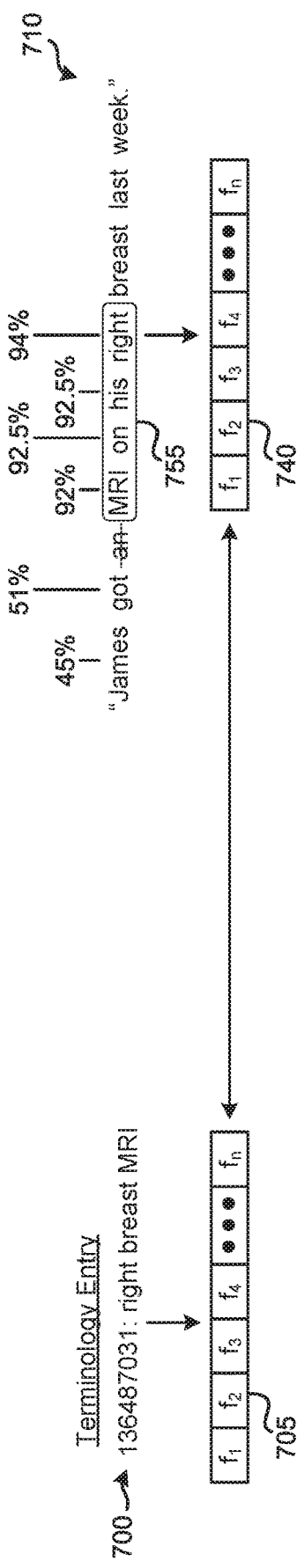

FIG. 7F illustrates the next stage in the example where unsupervised entity recognizer 600 has processed the next word in text 710. As shown in FIG. 7F, unsupervised entity recognizer 600 has identified the next word in text 710 ("right" in this example), increased the size of window of words 755 to the size of 4, and calculated a confidence score for medical terminology entry 700 with respect to the identified word based on embedding 705 for medical terminology entry 700 and word embedding 740 for words in window of words 755 (e.g., an average of word embeddings of each of the words in window of words 755). As the current identified word is "right" and the size of window of words 755 is 4, window of words 755 includes the words "MRI on his right". Since the calculated confidence score for the identified word (94% in this example) is not less than (i.e., greater than or equal to) the defined threshold score of 90% and is greater than or equal to the previous calculated confidence score (e.g., the confidence score calculated for the entry with respect to the word "his" in text 710), unsupervised entity recognizer 600 increases the size of the window of words to the value of 5, iterates to the next word in the sequence of raw and unstructured text, and calculates a confidence score for the next word.

At the seventh stage in the example illustrated in FIG. 7G, unsupervised entity recognizer 600 has processed the next word in text 710. As illustrated in FIG. 7G, unsupervised entity recognizer 600 has identified the next word in text 710 ("breast" in this example), increased the size of window of words 755 to the size of 5, and calculated a confidence score for medical terminology entry 700 with respect to the identified word based on embedding 705 for medical terminology entry 700 and word embedding 745 for words in window of words 755 (e.g., an average of word embeddings of each of the words in window of words 755). At this stage, window of words 755 includes the words "MRI on his right breast" because the current identified word is "breast" and the size of window of words 755 is 5. As the calculated confidence score for the identified word (95% in this example) is not less than (i.e., greater than or equal to) the defined threshold score of 90% and is greater than or equal to the previous calculated confidence score (e.g., the confidence score calculated for the entry with respect to the word "right" in text 710), unsupervised entity recognizer 600 increases the size of the window of words to the value of 6, iterates to the next word in the sequence of raw and unstructured text, and calculates a confidence score for the next word.

In the next stage in the example, as illustrated in FIG. 7H, unsupervised entity recognizer 600 has processed the next word in text 710. Unsupervised entity recognizer 600 has identified the next word in text 710 ("last" in this example), increased the size of window of words 755 to the size of 6, and calculated a confidence score for medical terminology entry 700 with respect to the identified word based on embedding 705 for medical terminology entry 700 and word embedding 750 for words in window of words 755 (e.g., an average of word embeddings of each of the words in window of words 755), as shown in FIG. 7H. Because the current identified word is "last" and the size of window of words 755 is 6, window of words 755 includes the words "MRI on his right breast last". The calculated confidence score for the identified word (82% in this example) is not less than (i.e., greater than or equal to) the defined threshold score of 90%. However, calculated confidence score for the identified word is not greater than or equal to (i.e., less than) the previous calculated confidence score (e.g., the confidence score calculated for the entry with respect to the word "breast" in text 710). Hence, unsupervised entity recognizer 600 determines that the previous window of words 755 is an entity, resets the size of the window of words to the default value of 1, iterates to the next word in the sequencer of raw and unstructured text, and calculates the confidence score for the next word. As illustrated in FIG. 7I, the previous window of words 755, which has a previous size of 5, is "MRI on his right breast". Unsupervised entity recognizer 600 determines these words in text 710 as constituting an entity.

FIG. 7J illustrates the last stage in the example where unsupervised entity recognizer 600 has processed the next word in text 710. As shown in FIG. 7J, unsupervised entity recognizer 600 has identified the next word in text 710 ("week" in this example), reset the size of window of words 755 to the default size of 1, and calculated a confidence score for medical terminology entry 700 with respect to the identified word based on embedding 705 for medical terminology entry 700 and word embedding 760 for words in window of words 755. Window of words 755 includes the word "week" as the current identified word is "week" and the size of window of words 755 is 1. As illustrated, the calculated confidence score for the identified word (79% in this example) is less than the defined threshold score of 90%. Since there are no more words left in text 710 to process, unsupervised entity recognizer 600 is done processing sequence of raw and unstructured text 710.

FIGS. 6 and 7A-7J illustrate an example of unsupervised entity recognizer 600 recognizing an entity in a sequence of raw and unstructured text based on one medical terminology entry stored in knowledge base storage 135. In some embodiments, unsupervised entity recognizer 600 performs the same process on text 710 for each medical terminology entry stored in knowledge base storage 135. Moreover, unsupervised entity recognizer 600 performs the same process on each sequence of raw and unstructured text in source documents 150 for each medical terminology entry stored in knowledge base storage 135.

Returning to FIG. 6, supervised entity recognizer 605 is responsible for recognizing entities in sequences of raw and unstructured text based on learned word embeddings. For example, when supervised entity recognizer 605 receives a sequence of raw and unstructured text, supervised entity recognizer 605 uses a ML model configured to recognizer entities to recognize entities in the sequence of raw and unstructured text. Such an ML model may be trained using sequences of raw and unstructured text that are annotated with correctly recognized entities.

Entity selector 615 is in charge of selecting an entity from several entities recognized by unsupervised entity recognizer 600, supervised entity recognizer 605, and third-party entity recognizer 610. For example, for a given sequence of raw and unstructured text in a source document 150, entity selector 615 may receive from unsupervised entity recognizer 600 a first entity recognized by unsupervised entity recognizer 600, a second entity recognized by supervised entity recognizer 605, and a third entity recognized by third-party entity recognizer 610. In some cases there may be conflicts between the entities recognized by unsupervised entity recognizer 600, supervised entity recognizer 605, and third-party entity recognizer 610. In some such cases, entity selector 615 selects the entity recognized by unsupervised entity recognizer 600 as the entity recognize for the sequence of raw and unstructured text. In other cases, some of the entity recognizers 600-610 may recognize an entity in a sequence of raw and unstructured text while some of the other entity recognizers 600-610 may not recognize any entities in the sequence of raw and unstructured text. If unsupervised entity recognizer 600 has recognized an entity, entity selector 615 selects the entity recognized by unsupervised entity recognizer 600. If supervised entity recognizer 605 and third-party entity recognizer 610 each have recognized an entity in the sequence of raw and unstructured text, entity selector 615 selects the recognized entity with the higher confidence score.

Figure 8:
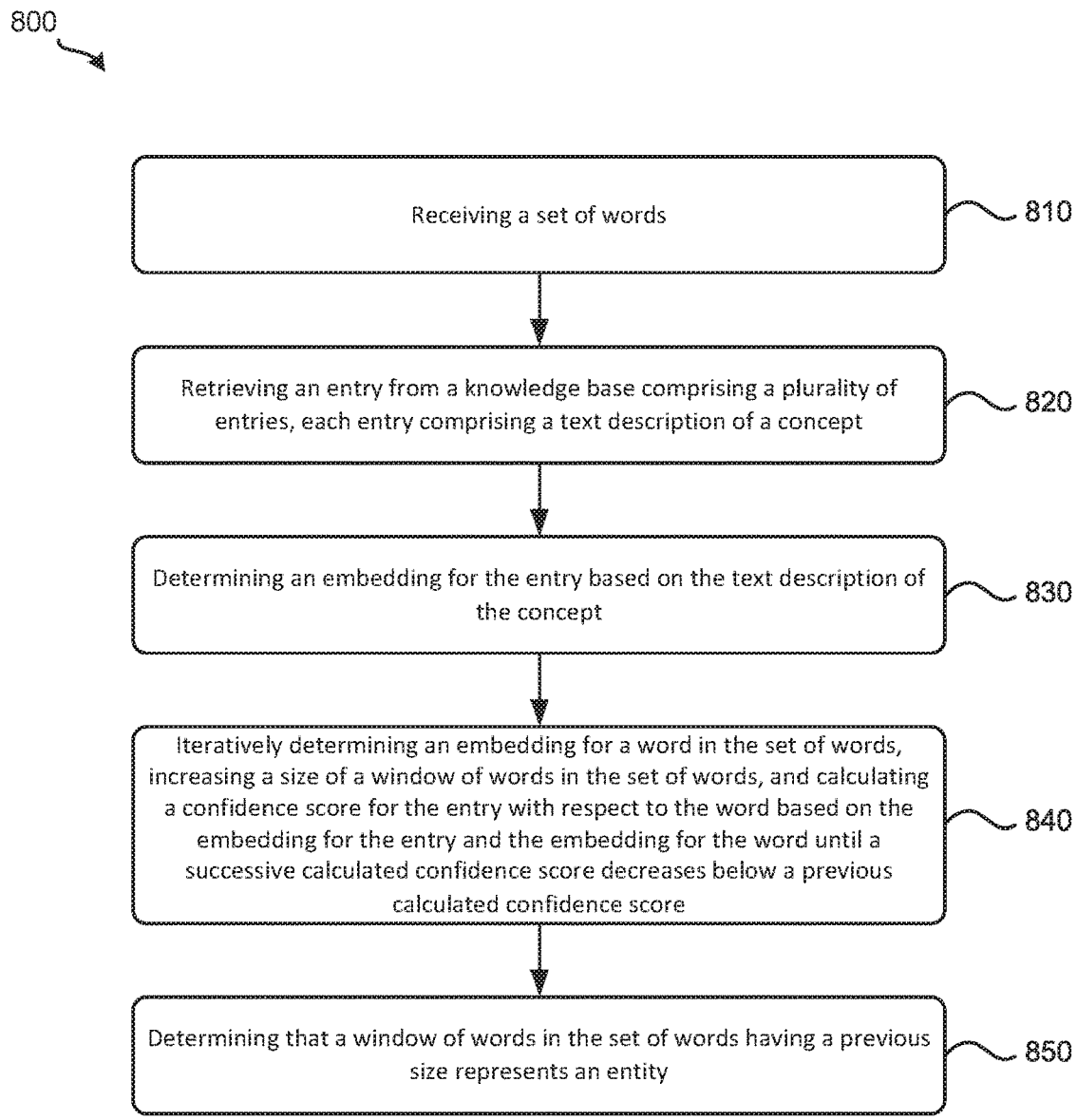
FIG. 8 illustrates a process for recognizing an entity in raw text according to some embodiments.

FIG. 8 illustrates a process 800 for recognizing an entity in raw text according to some embodiments. In some embodiments, entity recognizer 115 performs process 800. Process 800 begins by receiving, at 810, a set of words. Referring to FIGS. 6 and 7A as an example, unsupervised entity recognizer 600 may receive sequence of raw and unstructured text 710 from a source document 150 stored in source documents storage 145.

Next, process 800 retrieves, at 820, an entry from a knowledge base comprising a plurality of entries. Each entry comprises a text description of a concept. Referring to FIGS. 6 and 7A as an example, unsupervised entity recognizer 600 retrieves medical terminology entry 700 from knowledge base storage 135. As shown in FIG. 7A, medical terminology entry 700 includes a text description of a concept ("right breast MRI").

Process 800 then determines, at 830, an embedding for the entry based on the text description of the concept. Referring to FIGS. 1 and 7A as an example, word embedding manager 105 generated embedding 705 for medical terminology entries 700 by determining a word embedding for each word in the text description of the medical terminology entry 700 and calculated an average of the determined word embeddings for the words in the text description of the medical terminology entry 700.

After operation 840, process 800 iteratively determines, at 840, an embedding for a word in the set of words, increases a size of a window of words in the set of words, and calculates a confidence score for the entry with respect to the word based on the embedding for the entry and the embedding for the word until a successive calculated confidence score decreases below a previous calculated confidence score. Referring to FIGS. 6 and 7C-7H as an example, unsupervised entity recognizer 600 iteratively determines an embedding for a word in text 710, increases a size of window of words 755 in text 710, and calculates a confidence score for medical terminology entry 700 with respect to the word based on embedding 705 for medical terminology entry 700 and the embedding for the word until a successive calculated confidence score decreases below a previous calculated confidence score. As shown in FIG. 7H, the calculated confidence score for medical terminology entry 700 with respect to identified word "last" decreased below the previous calculated confidence score for medical terminology entry 700 with respect to the word "breast".

Finally, process 800 determines, at 850, that a window of words in the set of words having a previous size represents an entity. Referring to FIGS. 6 and 7I as an example, because the calculated confidence score for medical terminology entry 700 with respect to identified word "last" decreased below the previous calculated confidence score for medical terminology entry 700 with respect to the word "breast", unsupervised entity recognizer 600 determines that the previous window of words 755 "MRI on his right breast," which has a previous size of 5, is an entity.

4. Unknown Word Manager

Figure 9:
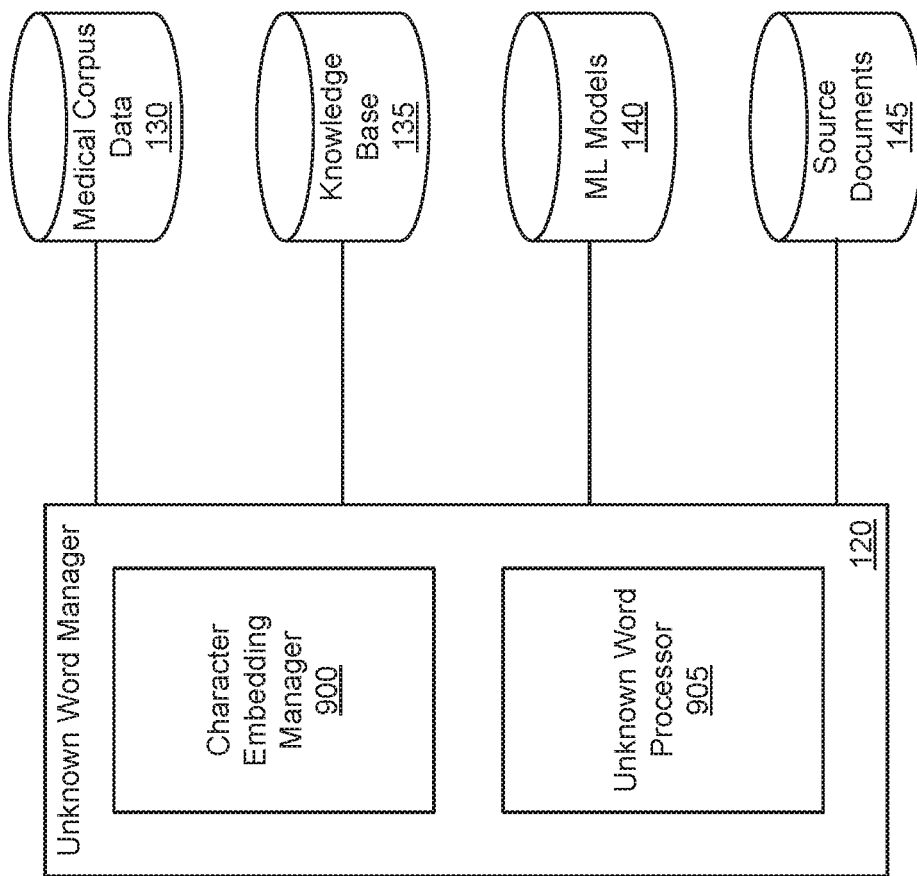
FIG. 9 illustrates an architecture of the unknown word manager illustrated in FIG. 1 according to some embodiments.

FIG. 9 illustrates an architecture of unknown word manager 120 according to some embodiments. As explained above, unknown word manager 120 is responsible for determining word embeddings for unknown words. An unknown word is a word that does not have a learned word embedding in some embodiments. In other words, an unknown word is a word that is not included in the corpus of data that word embedding manager 105 used to train word embeddings. Unknown word manager 120 can use character embeddings to determine whether an unknown word is similar to another word (e.g., a known word). In some embodiments, a character embedding is a vector representation of a string of characters having a defined length in a vector space. When unknown word manager 120 finds a known word that is similar to an unknown word, unknown word manager 120 can use the word embedding for the known word as the word embedding for the unknown word. This way, an embedding for a sequence of raw and unstructured text that includes an entity and an unknown word can be calculated and, thus, an entry in knowledge base storage 135 can be determined for the entity.

As shown in FIG. 9, unknown word manager 120 includes character embedding manager 900 and unknown word processor 905. Character embedding manager 900 is configured to manage character embeddings. For example, character embedding manager 900 may generate different sets of character embeddings for different character lengths. To generate character embeddings for a particular character length, character embedding manager 900 generates an ML model (e.g., a neural network) that includes character embeddings for strings of a defined length of characters. Character embedding manager 900 then initializes the values of the character embeddings in the ML model to a random set of values. Next, character embedding manager 900 uses the medical data stored in medical corpus data storage 130 and a filter that is the same size as the defined character length to train the character embeddings in the ML model.

In some embodiments, character embedding manager 900 uses technique similar to a skip-gram technique to train the ML model except instead of using words as the inputs and outputs of the ML model, character embedding manager 900 uses strings of the defined length of characters. Other techniques to train the ML model are possible. Character embedding manager 900 trains the ML model until a defined threshold convergence is reached. In some embodiments, a character embedding for a string of the defined length of characters may be determined by accessing the ML model and retrieving the character embedding. In other embodiments, character embedding manager 900 stores the learned character embeddings in a storage (not shown). In some such other embodiments, a character embedding for a string of the defined length of characters may be determined by accessing the storage and retrieving the character embedding.

Figure 10E:
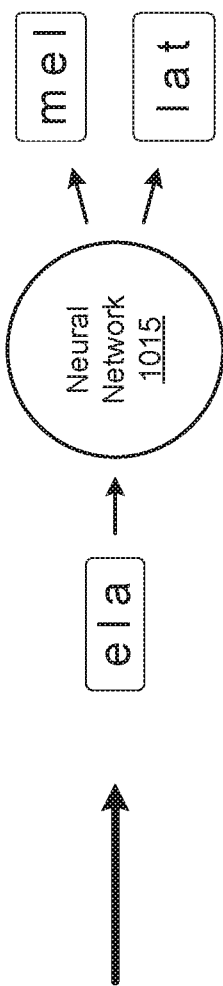

FIGS. 10A-10H illustrate an example of training character embeddings according to some embodiments. In particular, FIGS. 10A-10H illustrate training character embeddings for a character length of 3 characters using an example word 1000 in the medical data stored in medical corpus data storage 130. As shown in FIG. 10A, the example word 1000 is "melatonin". Before using word 1000 to for training character embeddings, character embedding manager 900 pads word 1000 with a defined number of space characters before and after word 1000. In some embodiments, the defined number of space characters used is one less than the character length. As the character length in this example is 3, the defined number of space characters is 2 (3−1). As shown in FIG. 10A, two spaces are added before and after word 1000 to form padded word 1005.

For this example, as illustrated in FIG. 10B, character embedding manager 900 has generated neural network 1015 that is configured to train character embeddings in neural network 1015 for a character length of 3 characters. FIG. 10B also illustrates the first stage of the example of training character embeddings using word 1000. Here, character embedding manager 900 uses filter 1010, a 3-character filter, to identify a string of the first three characters in padded word 1005 ("_m" in this example) as the input for neural network 1015. Character embedding manager 900 then identifies the next string of three characters in padded word 1005 ("_me" in this example), as indicated by the dotted rectangle, as the output for neural network 1015. The input and output are used to train the character embeddings in neural network 1015.

In the next stage of the example illustrated in FIG. 10C, character embedding manager 900 shifts filter 1010 one character to the right to identify a string of the second three characters in padded word 1005 ("_me" in this example) as the input for neural network 1015. Next, character embedding manager 900 identifies the previous string of three characters in padded word 1005 ("_m" in this example) and the next string of three characters in padded word 1005 ("mel" in this example), as indicated by the dotted rectangles, as the outputs for neural network 1015. The input and outputs are then used to train the character embeddings in neural network 1015.

FIG. 10D illustrates the fourth stage of the example where character embedding manager 900 has shifted filter 1010 one character to the right to identify a string of the third three characters in padded word 1005 ("mel" in this example) as the input for neural network 1015. Character embedding manager 900 continues by identifying the previous string of three characters in padded word 1005 ("_me" in this example) and the next string of three characters in padded word 1005 ("ela" in this example), as indicated by the dotted rectangles, as the outputs for neural network 1015. The input and outputs are used to train the character embeddings in neural network 1015.

At the next stage of the example shown in FIG. 10E, character embedding manager 900 has shifted filter 1010 one character to the right to identify a string of the third three characters in padded word 1005 ("ela" in this example) as the input for neural network 1015. Next, character embedding manager 900 identifies the previous string of three characters in padded word 1005 ("mel" in this example) and the next string of three characters in padded word 1005 ("lat" in this example), as indicated by the dotted rectangles, as the outputs for neural network 1015. The input and outputs are then used to train the character embeddings in neural network 1015.

Figure 10F:
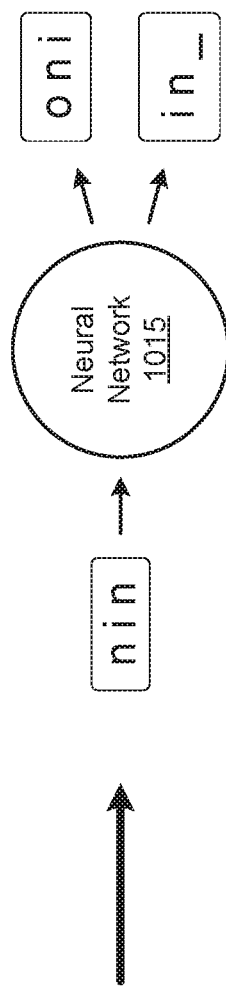

FIG. 10F illustrates the example after character embedding manager 900 has iteratively shifted filter 1010 one character to the right and used the identified three-character strings as inputs and outputs to train neural network 1015 in the same manner that described in the previous stages. Here, character embedding manager 900 is using filter 1010 to identify a string of the ninth three characters in padded word 1005 ("nin" in this example) as the input for neural network 1015. Character embedding manager 900 then identifies the previous string of three characters in padded word 1005 ("oni" in this example) and the next string of three characters in padded word 1005 ("in_" in this example), as indicated by the dotted rectangles, as the outputs for neural network 1015. The input and outputs are used to train the character embeddings in neural network 1015.

Figure 10G:
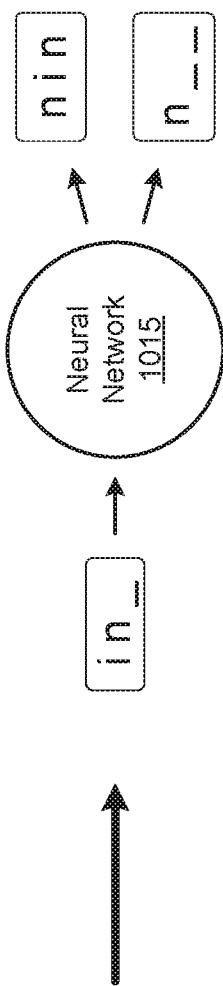

At the next stage of the example shown in FIG. 10G, character embedding manager 900 has shifted filter 1010 one character to the right to identify a string of the tenth three characters in padded word 1005 ("in_" in this example) as the input for neural network 1015. Character embedding manager 900 proceeds to identify the previous string of three characters in padded word 1005 ("nin" in this example) and the next string of three characters in padded word 1005 ("n_" in this example), as indicated by the dotted rectangles, as the outputs for neural network 1015. The input and outputs are then used to train the character embeddings in neural network 1015.

Figure 10H:
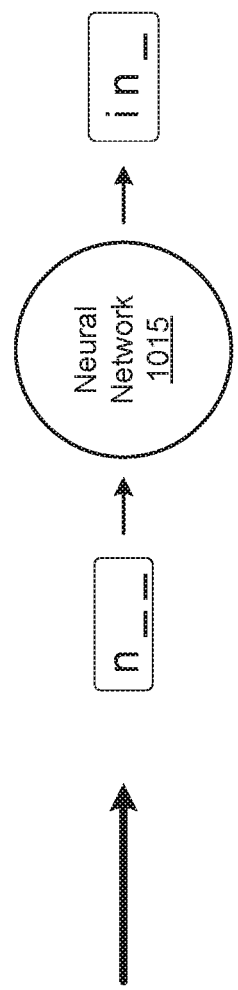

In the last stage of the example, as illustrated in FIG. 10H, character embedding manager 900 has shifted filter 1010 one character to the right to identify a string of the last three characters in padded word 1005 ("n_" in this example) as the input for neural network 1015. Next, character embedding manager 900 identifies the previous string of three characters in padded word 1005 ("in_" in this example), as indicated by the dotted rectangle, as the output for neural network 1015. The input and output are used to train the character embeddings in neural network 1015.

FIGS. 10A-10H illustrate an example of training character embeddings for a character length of 3 characters using a word in the medical data stored in medical corpus data storage 130. In some embodiments, character embedding manager 900 trains neural network 1015 with every word in the medical data stored in medical corpus data storage 130 using the same technique described above by reference to FIGS. 9 and 10A-10H. As explained above, character embedding manager 900 may generate different sets of character embeddings for different character lengths. For instance, in some embodiments, character embedding manager 900 uses the same technique described above by reference to FIGS. 9 and 10A-10H to generate two-character character embeddings, four-character character embeddings, five-character character embeddings, etc. In some embodiments, character embeddings manager 900 generate different sets of character embeddings for the same character lengths. Different sets of such character embeddings can be trained to learn different character features (e.g., prefixes, suffixes, roots, etc.).

Unknown word processor 905 handles the processing of unknown words. For example, unknown word processor 905 may receive from word embedding manager 105, concept manager 200, or context manager 205a request for a word embedding for an unknown word. In response, unknown word processor 905 determines to use a set of character embeddings for a particular character length. Then, unknown word processor 905 uses a window of characters that is the same size as the particular character length to iterate through strings in the unknown word, determine character embeddings for the strings, and determine a word embedding for the unknown word based on the character embeddings. Next, unknown word processor 905 performs the same process for all known words (e.g., all the words in the medical data stored in medical corpus data storage 130) and calculates vector distances (e.g., cosine similarities) between the determined word embedding for the unknown word and the word embeddings determined for each of the known words. Unknown word processor 905 repeats this whole process for other sets of character embeddings for other character lengths. Based on all the calculated vector distances, unknown word processor 905 determines the known word with the determined word embedding that is closest to the determined word embedding for the unknown word. Unknown word processor 905 uses the learned word embedding for the determined known word as the word embedding for the unknown word.

Figure 11A:
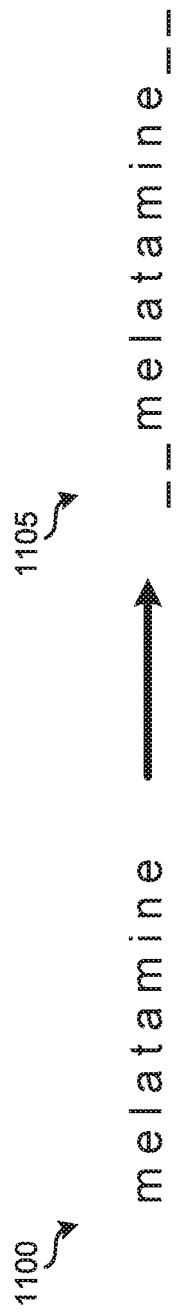

FIGS. 11A-11H illustrate an example of determining a word embedding for an unknown word based on character embeddings according to some embodiments. Specifically, FIGS. 11A-11H illustrate determining a word embedding for unknown word 1100 based on character embeddings for a character length of 3 characters. As illustrated in FIG. 11A, the unknown word 1100 is "melatamine". First, unknown word processor 905 pads unknown word 1100 with a defined number of space characters before and after unknown word 1100. In some embodiments, the defined number of space characters used is one less than the character length. Since the character length for this example is 3, the defined number of space characters is 2 (3–1). As shown in FIG. 11A, two spaces are added before and after unknown word 1100 to form padded unknown word 1105.

Figure 11B:
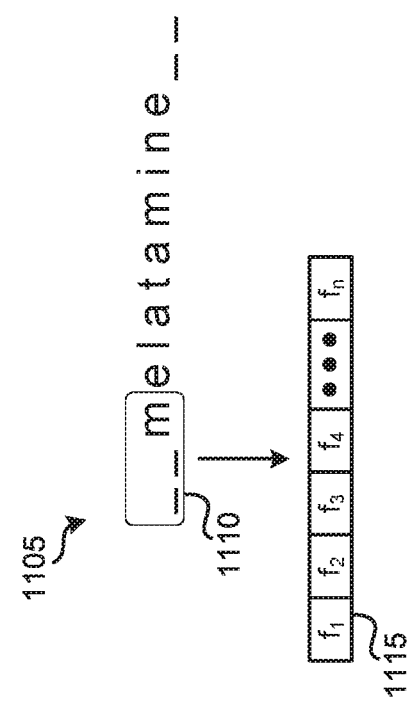

In the first stage of the example as shown in FIG. 11B, unknown word processor 905 uses window of characters 1110 to identify a string of the first three characters in padded unknown word 1105 ("_m" in this example). As mentioned above, unknown word processor 905 is determining a word embedding based on character embeddings for a character length of 3 characters. Therefore, the size use for window of characters 1110 is three characters. Next, unknown word processor 905 determines a three-character character embedding 1115 for the identified string by retrieving the character embedding for the identified string from the ML model used to train the three-character character embeddings (e.g. neural network 1015) or the storage used to store the learned three-character character embeddings.

FIG. 11C illustrates the next stage of the example where unknown word processor 905 has shifted window of characters 1110 one character to the right to identify a string of the second three characters in padded unknown word 1105 ("_me" in this example). Unknown word processor 905 then determines a three-character character embedding 1120 for the identified string by retrieving the character embedding for the identified string from the ML model used to train the three-character character embeddings (e.g. neural network 1015) or the storage used to store the learned three-character character embeddings.

At the third stage of the example shown in FIG. 11D, unknown word processor 905 has shifted window of characters 1110 one character to the right to identify a string of the third three characters in padded unknown word 1105 ("mel" in this example). Unknown word processor 905 determines a three-character character embedding 1125 for the identified string by retrieving the character embedding for the identified string from the ML model used to train the three-character character embeddings (e.g. neural network 1015) or the storage used to store the learned three-character character embeddings.

Figure 11E:
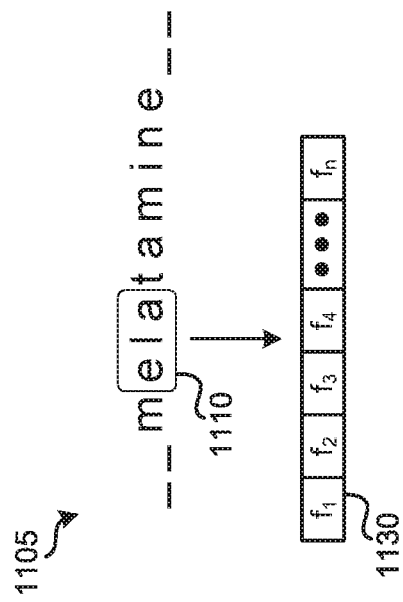

In the next stage of the example illustrated in FIG. 11E, unknown word processor 905 has shifted window of characters 1110 one character to the right to identify a string of the fourth three characters in padded unknown word 1105 ("ela" in this example). Next, unknown word processor 905 determines a three-character character embedding 1130 for the identified string by retrieving the character embedding for the identified string from the ML model used to train the three-character character embeddings (e.g. neural network 1015) or the storage used to store the learned three-character character embeddings.

Figure 11F:
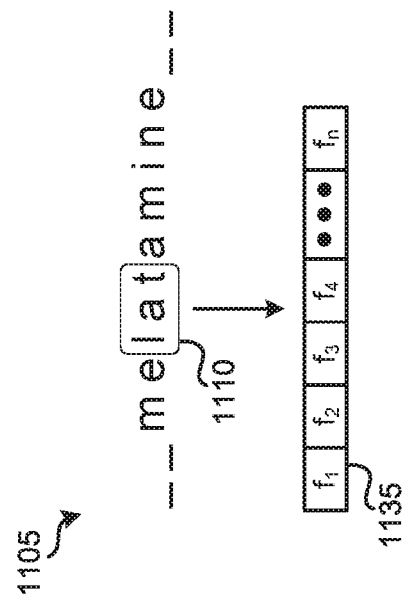

FIG. 11F illustrates the fifth stage of the example where unknown word processor 905 has shifted window of characters 1110 one character to the right to identify a string of the fifth three characters in padded unknown word 1105 ("lat" in this example). Unknown word processor 905 then determines a three-character character embedding 1135 for the identified string by retrieving the character embedding for the identified string from the ML model used to train the three-character character embeddings (e.g. neural network 1015) or the storage used to store the learned three-character character embeddings.

Figure 11G:
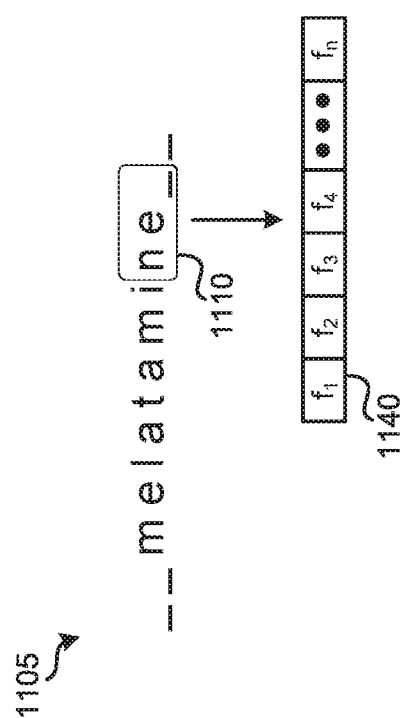

FIG. 11G illustrates the example after unknown word processor 905 has iteratively shifted window of characters 1110 one character to the right to identify a three-character string and determined a three-character character embedding for the identified three-character string. At the stage shown in FIG. 11G, unknown word processor 905 900 is using window of characters 1110 to identify a string of the eleventh three characters in padded unknown word 1105 ("ne_" in this example). Then, unknown word processor 905 determines a three-character character embedding 1140 for the identified string by retrieving the character embedding for the identified string from the ML model used to train the three-character character embeddings (e.g. neural network 1015) or the storage used to store the learned three-character character embeddings.

Figure 11H:
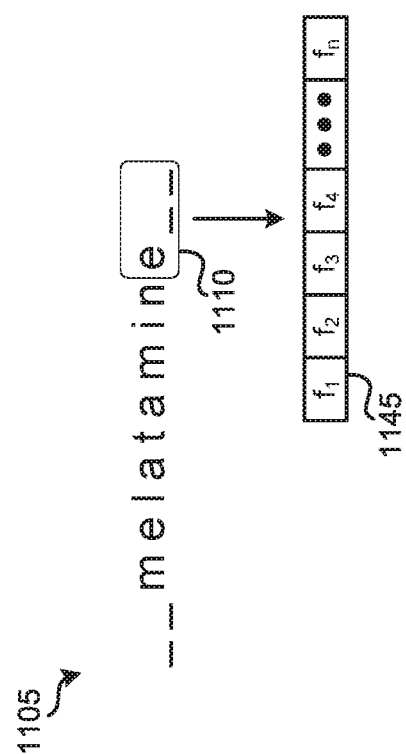

At the last stage of the example shown in FIG. 11H, unknown word processor 905 has shifted window of characters 1110 one character to the right to identify a string of the last three characters in padded unknown word 1105 ("e_" in this example). Next, unknown word processor 905 determines a three-character character embedding 1145 for the identified string by retrieving the character embedding for the identified string from the ML model used to train the three-character character embeddings (e.g. neural network 1015) or the storage used to store the learned three-character character embeddings.

After iterating through all the three-character strings in padded unknown word 1105, unknown word processor 905 determines a word embedding for unknown word 1100 by calculating an average of the determined three-character embeddings (i.e., character embedding 1115, character embedding 1120, character embedding 1125, etc.) for the three-character strings in padded unknown word 1105. Using the same set of three-character embeddings, unknown word processor 905 determines a word embedding for each known word (e.g., each word in the medical data stored in medical corpus data storage 130) and calculates vector distances (e.g., cosine similarities) between the determined word embedding for the unknown word and the word embeddings determined for each of the known words. Then, unknown word processor 905 repeats this whole process for other sets of character embeddings for other character lengths. Based on all the calculated vector distances, unknown word processor 905 determines the known word with the determined word embedding that is closest to the determined word embedding for the unknown word. Unknown word processor 905 uses the learned word embedding for the determined known word generated by word embedding manager 105 (not the word embedding that unknown word processor 905 determined based on character embeddings for strings in the known word) as the word embedding for the unknown word.

Figure 12:
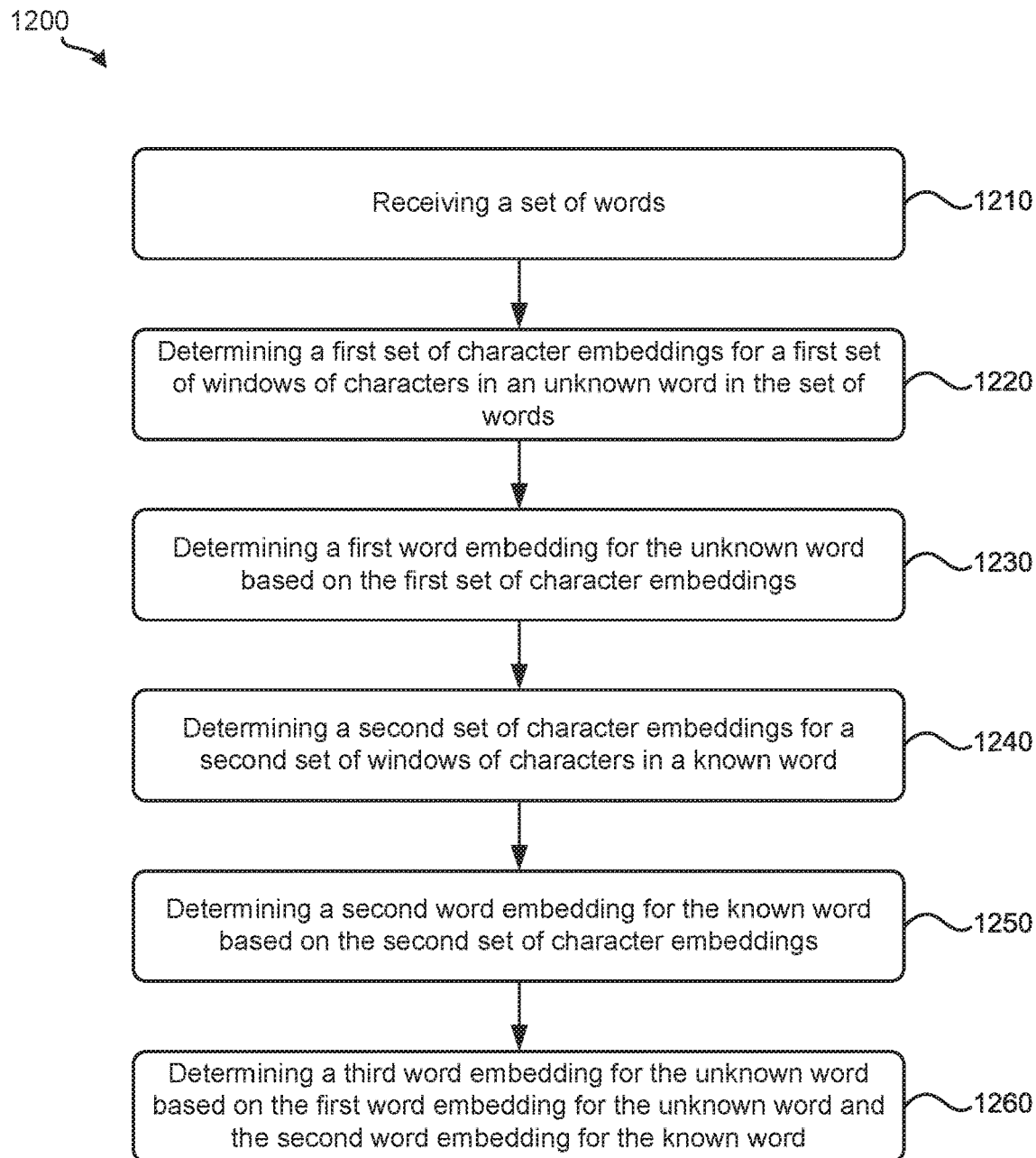
FIG. 12 illustrates a process for determining a word embedding for an unknown word based on character embeddings according to some embodiments.

FIG. 12 illustrates a process 1200 for determining a word embedding for an unknown word based on character embeddings according to some embodiments. In some embodiments, unknown word manager 120 performs process 1200. Process 1200 starts by receiving, at 1210, a set of words. Referring to FIGS. 1, 2, 9, and 11A as an example, unknown word processor 905 can receive unknown word 1100 from word embedding manager 105, concept manager 200, or context manager 205 along with a request to determine a word embedding for unknown word 1100.

Next, process 1200 determines, at 1220, a first set of character embeddings for a first set of windows of characters in an unknown word in the set of words. Referring to FIGS. 9 and 11B-11H as an example, unknown word processor 905 uses window of characters 1110 to identify three-character strings in padded unknown word 1105 and determine three-character character embeddings for the strings.

Process 1200 then determining, at 1230, a first word embedding for the unknown word based on the first set of character embeddings. Referring to FIGS. 9 and 11B-11H as an example, unknown word processor 905 determines a word embedding for unknown word 1100 based on determined three-character character embeddings for the identified three-character strings in padded unknown word 1105 (i.e., character embedding 1115, character embedding 1120, character embedding 1125, etc.).

After operation 1230, process 1200 determines, at 1240, a second set of character embeddings for a second set of windows of characters in a known word. Referring to FIGS. 9 and 11A as an example, unknown word processor 905 determines three-character character embeddings for a known word (e.g., a word in the medical data stored in medical corpus data storage 130) in the same fashion that unknown word processor 905 determined three-character character embeddings for unknown word 1100.

Next, process 1200 determines, at 1250, a second word embedding for the known word based on the second set of character embeddings. Referring to FIGS. 9 and 11A as an example, unknown word processor 905 determines a word embedding for the known word based on the three-character character embeddings for strings in the known word in the same way that unknown word processor 905 determined a word embedding for unknown word 1100 based on the three-character character embeddings for strings in padded unknown word 1105.

Finally, process 1200 determining, at 1260, a third word embedding for the unknown word based on the first word embedding for the unknown word and the second word embedding for the known word. Referring to FIG. 9 as an example, unknown word processor 905 calculated a vector distance (e.g., cosine similarity) between the determined word embedding for the known word and the determined word embedding for unknown word 1100 and determined that the word embedding for the known word is closest to the word embedding for unknown word 1100. As such, unknown word processor 905 determines the learned word embedding generated by word embedding manager 105 as the word embedding for unknown word 1100.

5. Custom Tags Manager

Figure 13:
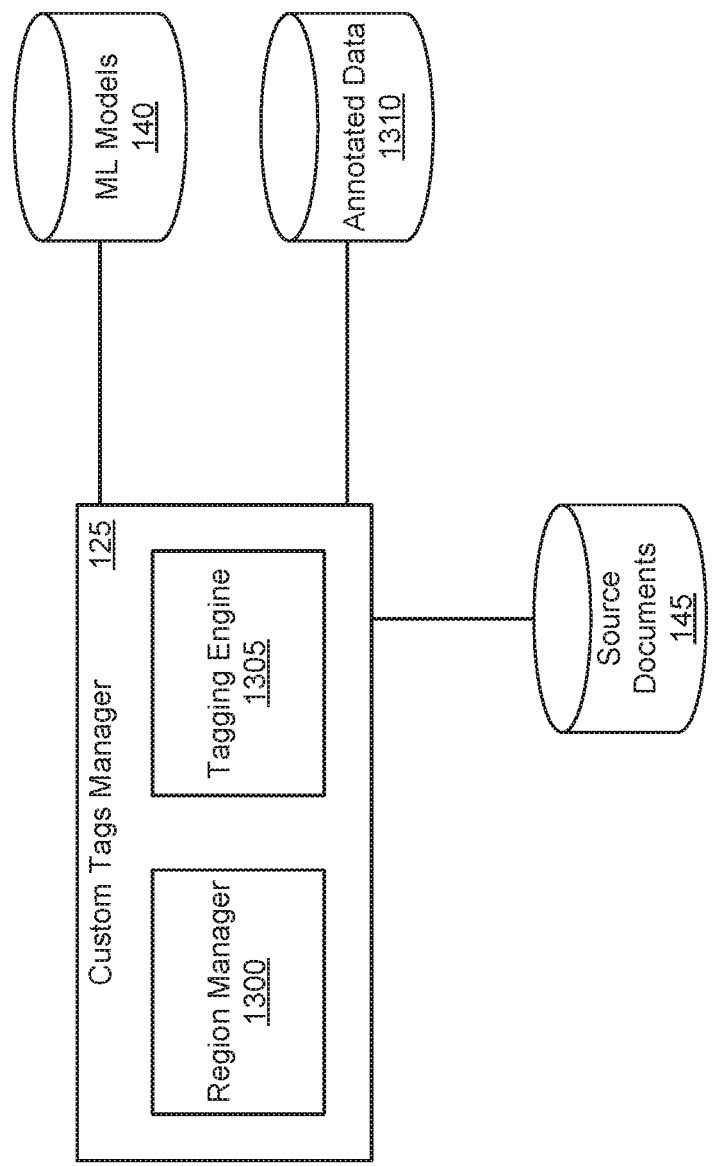
FIG. 13 illustrates an architecture of the custom tags manager illustrated in FIG. 1 according to some embodiments.

FIG. 13 illustrates an architecture of custom tags manager 125 illustrated in FIG. 1 according to some embodiments. As described above, custom tags manager 125 is in charge of managing custom-defined tags that are used to identify custom entity types. One of the limitations of entity recognizer 115 is that it may recognize set number of different types of entities. Custom tags allows any number of different types of entities may be identified.

As shown, custom tags manager 125 includes region manager 1300 and tagging engine 1305. Region manager 1300 is configured to manage regions in the vector space for the word embeddings (e.g., the vector space of the word embeddings generated by word embedding manager 105). For example, region manager 1300 can receive several different samples of sequences of words that are annotated as representing the same type of custom entity from annotated data storage 1310. In response to receiving these samples of sequences of words, region manager 1300 defines a region in the vector space for the word embeddings and stores it in ML models storage 140.

Figure 14A:
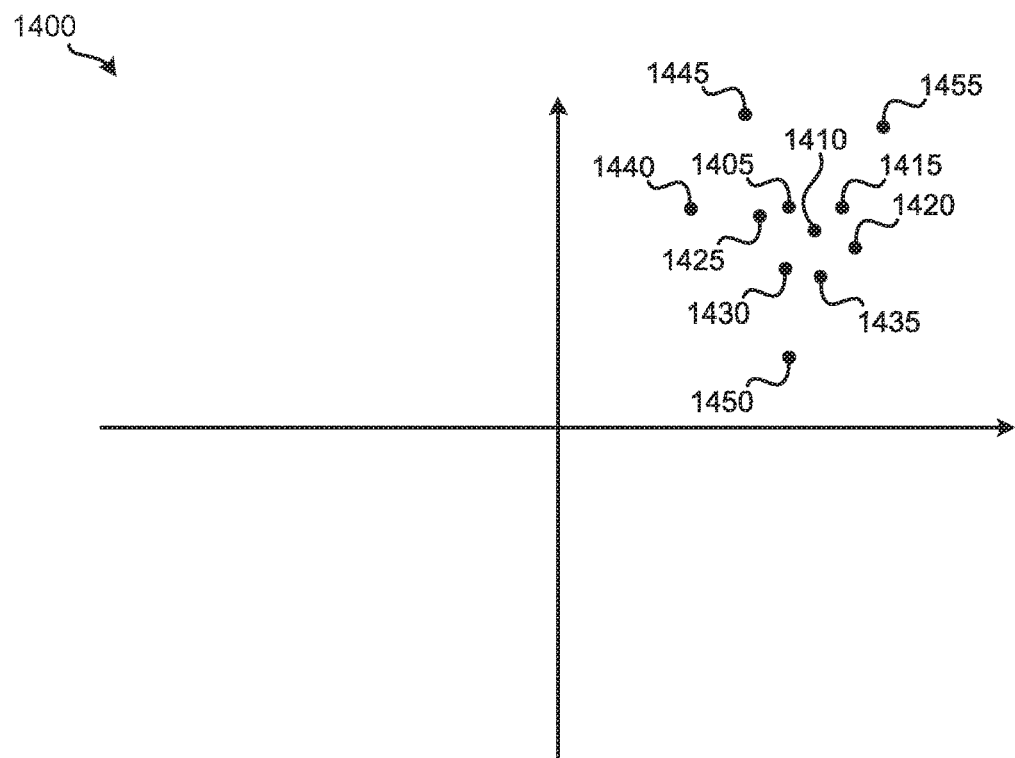
FIGS. 14A-14C illustrate an example of a region in a vector space for a custom tag according to some embodiments.
Figure 14B:
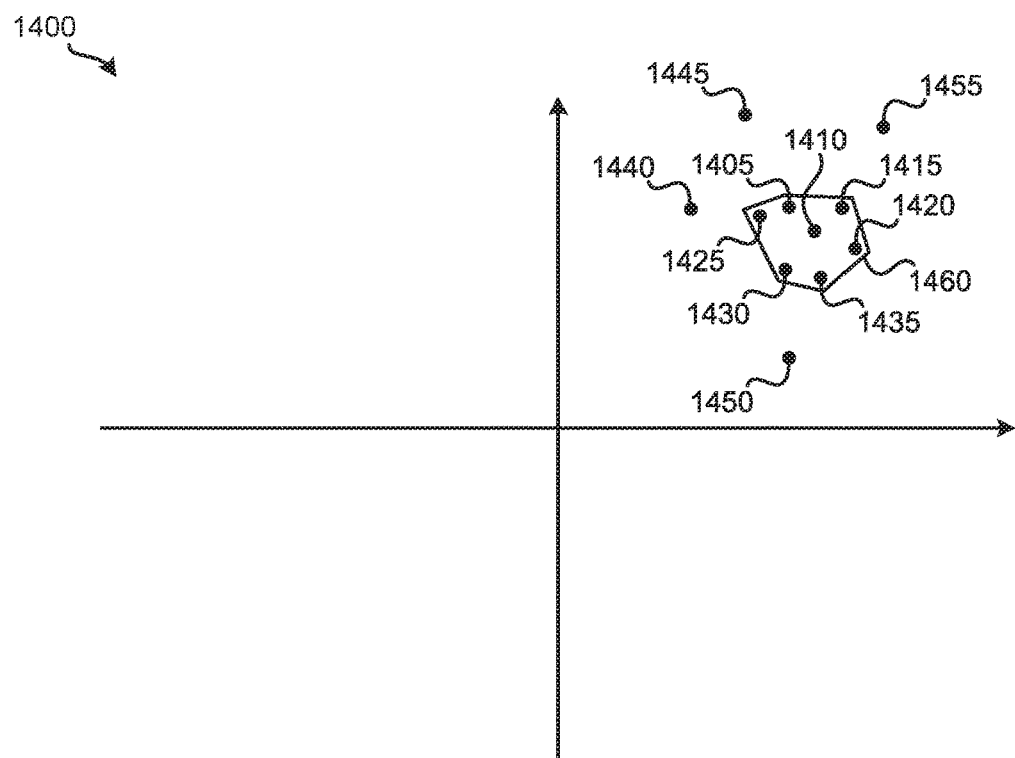
Figure 14C:
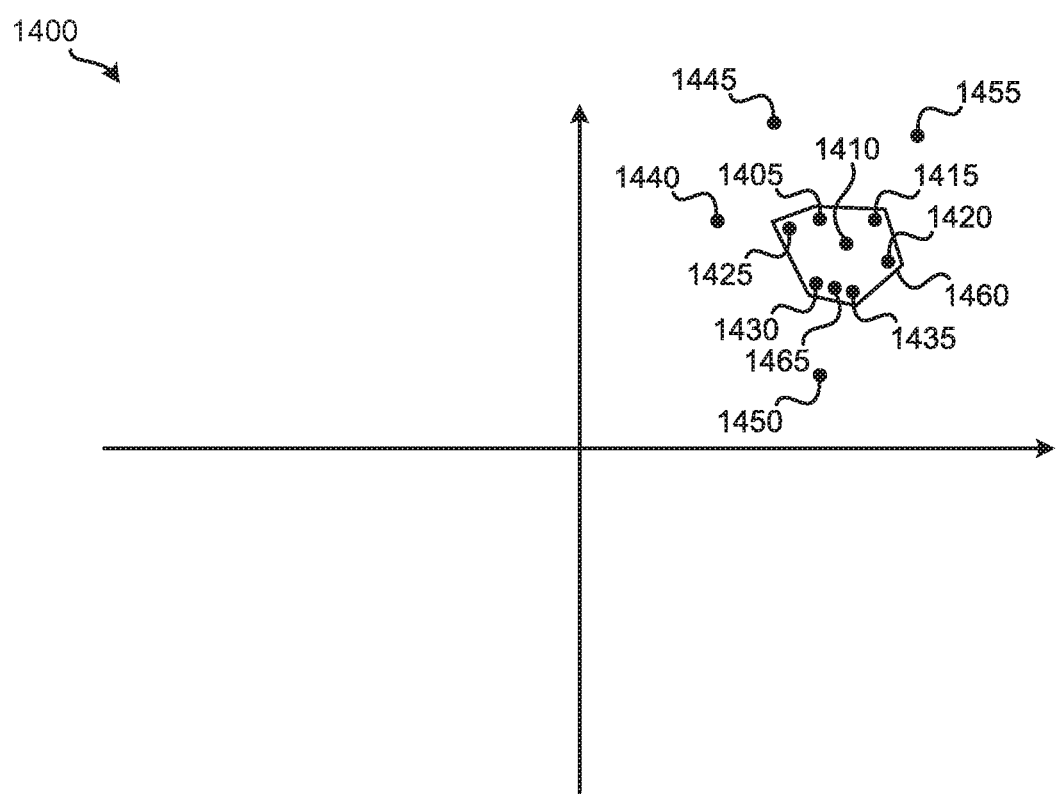

FIGS. 14A-14C illustrate an example of a region in a vector space for a custom tag according to some embodiments. In particular, FIGS. 14A-14C illustrate a region defined based on different samples of sequences of words that are annotated as representing the same type of custom entity. Referring to FIG. 14A, a two-dimensional vector space 1400 that includes word embeddings 1405-1450 is shown. For this example, words in the samples of sequences of words that region manager 1300 receives from annotated data storage 1310 are annotated as representing an entity that is an over-the-counter (OTC) medication. For instance, one of the sequence of words is "John took Aspirin" with "Aspirin" annotated as representing an entity that is an OTC medication. Another sequence of words is "Mary took Allegra" with "Allegra" annotated as representing an entity that is an OTC medication. Yet another sequence of words is "Jane took Tylenol" with "Tylenol" annotated as representing an entity that is an OTC medication. The word embeddings that region manager 1300 determines for the words in the samples of sequences of words annotated as representing an entity that is an OTC medication are represented by word embeddings 1405-1435 in this example. Word embedding 1440-1450 represent entities that are medications that are not OTC medication (e.g. Warfarin, Oxycodone, Penicillin, etc.).

FIG. 14B illustrates a region 1460 that has been defined for an "OTC medication" custom tag based on word embeddings 1405-1435 for the samples of sequences of words annotated as representing an entity that is an OTC medication. In this example, region manager 1300 defines region 1460 by generating a convex hull formed by word embeddings 1405-1435 in vector space 1400 and defining a boundary of a region encompassing the convex hull that is within a threshold distance of the boundary of the convex hull. Region manager 1300 uses the boundary of the region encompassing the convex hull as region 1460. Next, region manager 1300 stores region 1460 in ML models storage 140.

Returning to FIG. 13, tagging engine 1305 is responsible for identifying entities in sequences of raw and unstructured text based on custom tags. For instance, when tagging engine 1305 receives a sequence of raw and unstructured text in a source document 150 stored in source documents storage 145, tagging engine 1305 retrieves a region defined for a custom tag from ML models storage 140. Tagging engine 1305 then determines a word embedding for a word in the sequence of raw and unstructured text (e.g., by retrieving the word embedding for the word from the ML model used to train the word embeddings or the storage used to store the learned word embeddings, or by sending a request to unknown word manager 120 if the word is an unknown word) and determines whether the word embedding for the word falls within the region defined for the custom tag. If so, tagging engine 1305 tags the word as representing an entity defined by the custom tag. Tagging engine 1305 repeats this for each word in the sequence of raw and unstructured text. For each region defined for a custom tag stored in ML models storage, tagging engine 1305 performs the same process. As such, the same word in the sequence of raw and unstructured text may be tagged with multiple different custom tags.

FIG. 14C illustrates an example of tagging a word in a sequence of raw and unstructured text with a custom tag. For this example, the sequence of raw and unstructured text is "Bill took Ibuprofen" and tagging engine 1305 retrieved region 1460 from ML model storage 140. Word embedding 1465, as shown in FIG. 14C, is the word embedding that tagging engine 1305 determined for the word "Ibuprofen" in the sequence of raw and unstructured text. Tagging engine 1305 tags "Ibuprofen" with the custom tag "OTC medication" since word embedding 1465 is within region 1460, as illustrated in FIG. 14C.

FIGS. 14A-14C illustrate an example of a defining a region for a custom tag in a two-dimensional vector space and using the region to determine whether to tag a word with the custom tag. This example is used for purposes of simplicity and explanation. One of ordinary skill in the art will appreciate that the same technique may be equally applicable for vector spaces having any number of dimensions.

Figure 15:
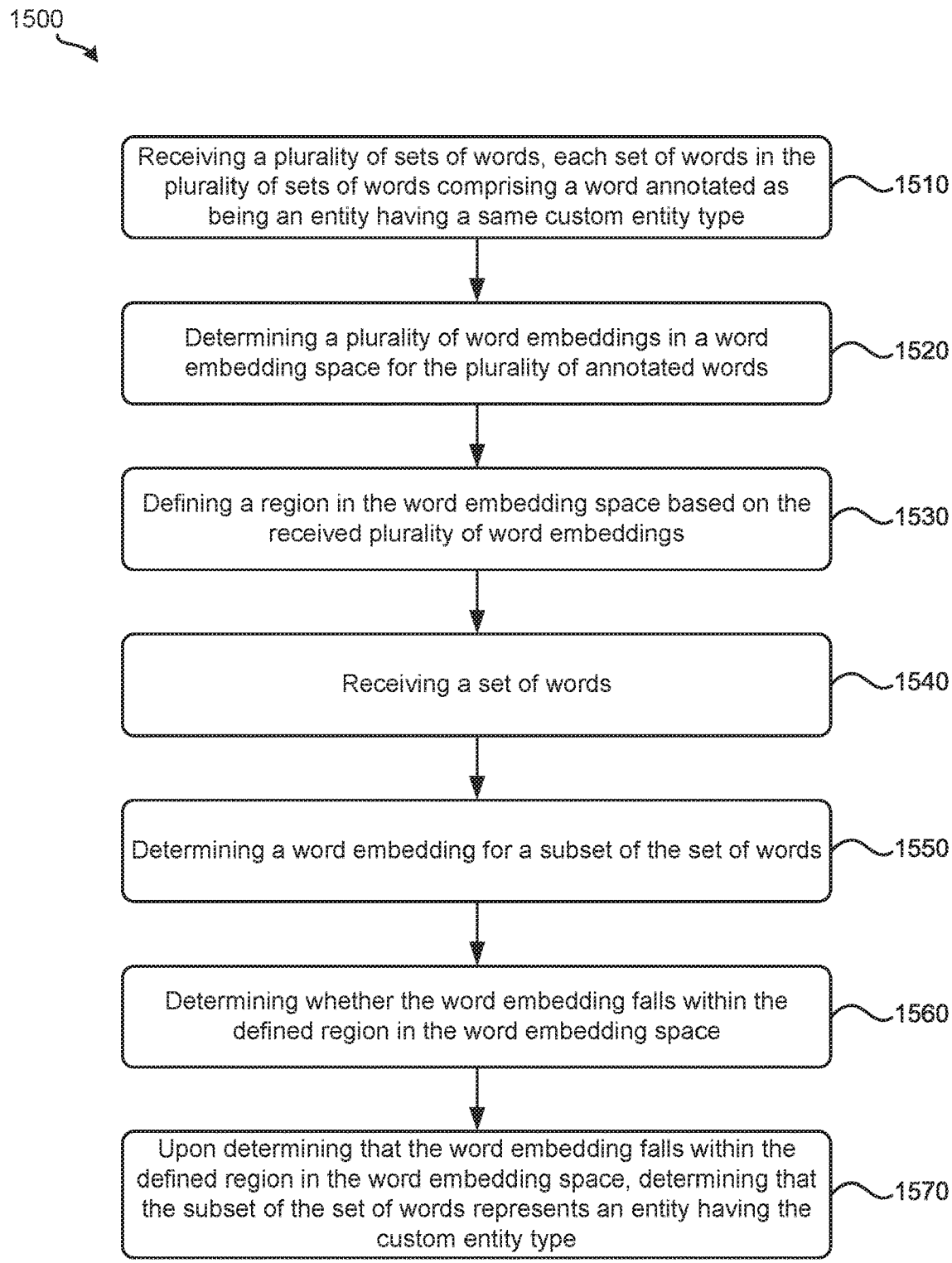
FIG. 15 illustrates a process for tagging a set of words with a custom tag according to some embodiments.

FIG. 15 illustrates a process 1500 for tagging a set of words with a custom tag according to some embodiments. In some embodiments, custom tags manager 125 performs process 1500. Process 1500 begins by receiving, at 1510, a plurality of sets of words. Each set of words in the plurality of sets of words comprises a word annotated as being an entity having a same custom entity type. Referring to FIGS. 13 and 14A as an example, region manager 1300 receives from annotated data storage 1310 several different samples of sequences of words that are annotated as representing an over-the-counter (OTC) medication.

Next, process determines, at 1520, a plurality of word embeddings in a word embedding space for the plurality of annotated words. Referring to FIGS. 13 and 14A as an example, region manager 1300 determines word embeddings 1405-1435 for the words in the samples of sequences of words annotated as representing an entity that is an OTC medication. Process 1500 then defines, at 1530, a region in the word embedding space based on the received plurality of word embeddings. Referring to FIGS. 13 and 14B as an example, region manager 1300 has defined region 1460 for an "OTC medication" custom tag based on word embeddings 1405-1435 by generating a convex hull formed by word embeddings 1405-1435 in vector space 1400 and defining a boundary of a region encompassing the convex hull that is within a threshold distance of the boundary of the convex hull. Region manager 1300 uses the boundary of the region encompassing the convex hull as region 1460.

After operation 1530, process 1500 receives, at 1540, a set of words. Referring to FIGS. 13 and 14C as an example, tagging engine 1305 receives a sequence of raw and unstructured text that is "Bill took Ibuprofen". Next, process 1500 determines, at 1550, a word embedding for a subset of the set of words. Referring to FIGS. 13 and 14C as an example, tagging engine 1305 determines word embedding 1465 for the word "Ibuprofen" in the sequence of raw and unstructured text.

Process 1500 then determines, at 1560, whether the word embedding falls within the defined region in the word embedding space. Referring to FIGS. 13 and 14C as an example, tagging engine 1305 determines whether word embedding 1465 falls within region 1460. Finally, upon determining that the word embedding falls within the defined region in the word embedding space, process 1500 determines, at 1570, that the subset of the set of words represents an entity having the custom entity type. Referring to FIGS. 13 and 14C as an example, tagging engine 1305 tags the word "Ibuprofen" in the sequence of raw and unstructured text with the custom tag "OTC medication" because word embedding 1465 is within region 1460.

6. Example Systems

Figure 16:
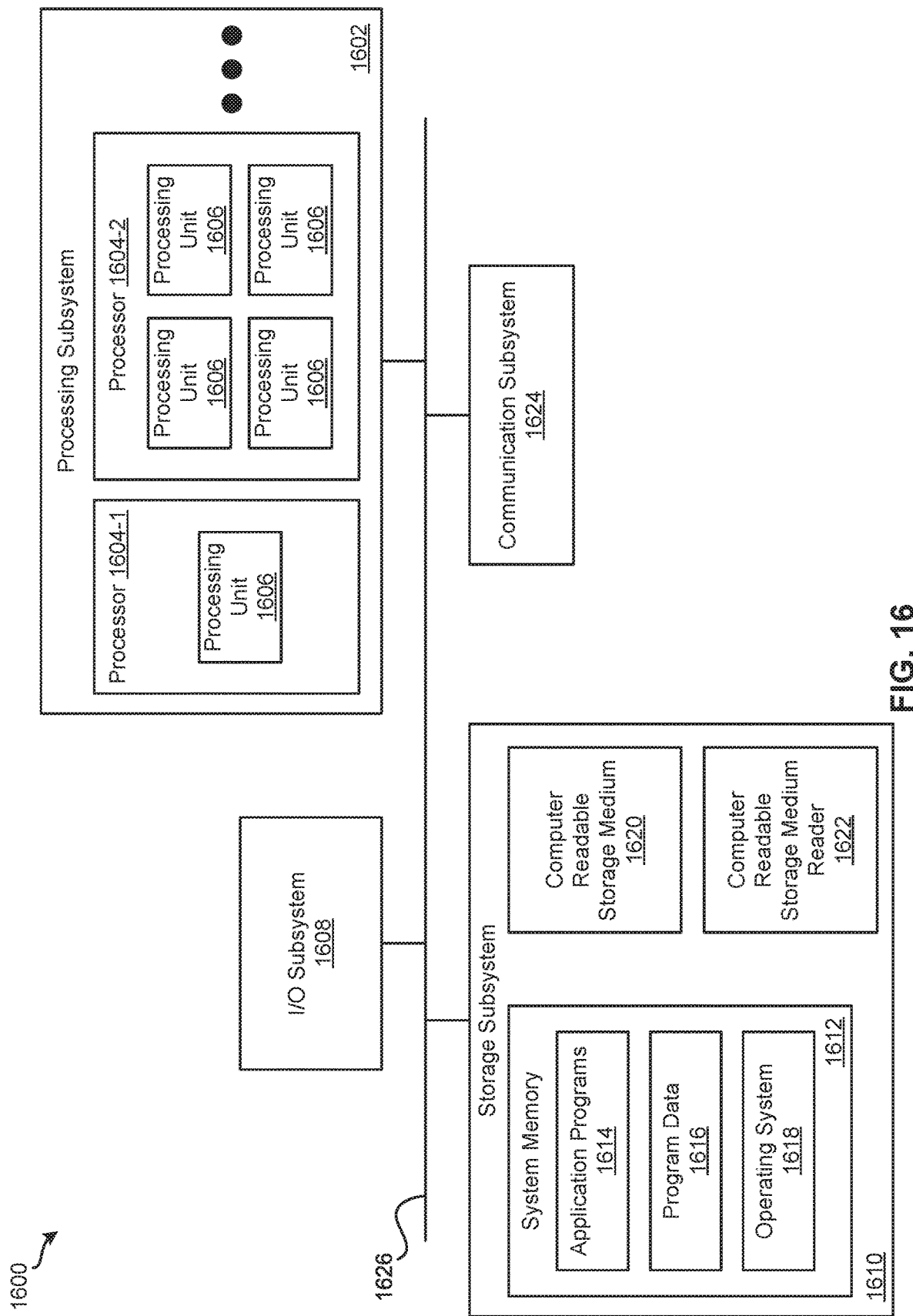
FIG. 16 illustrates an exemplary computer system, in which various embodiments may be implemented.

FIG. 16 illustrates an exemplary computer system 1600 for implementing various embodiments described above. For example, computer system 1600 may be used to computing systems 100. Computer system 1600 may be a desktop computer, a laptop, a server computer, or any other type of computer system or combination thereof. Some or all elements of word embedding manager 105, terminology manager 110, entity recognizer 115, unknown word manager 120, custom tags manager 125, or combinations thereof can be included or implemented in computer system 1600. In addition, computer system 1600 can implement many of the operations, methods, and/or processes described above (e.g., process 500, process 800, process 1200, and process 1500). As shown in FIG. 16, computer system 1600 includes processing subsystem 1602, which communicates, via bus subsystem 1626, with input/output (I/O) subsystem 1608, storage subsystem 1610 and communication subsystem 1624.

Bus subsystem 1626 is configured to facilitate communication among the various components and subsystems of computer system 1600. While bus subsystem 1626 is illustrated in FIG. 16 as a single bus, one of ordinary skill in the art will understand that bus subsystem 1626 may be implemented as multiple buses. Bus subsystem 1626 may be any of several types of bus structures (e.g., a memory bus or memory controller, a peripheral bus, a local bus, etc.) using any of a variety of bus architectures. Examples of bus architectures may include an Industry Standard Architecture (ISA) bus, a Micro Channel Architecture (MCA) bus, an Enhanced ISA (EISA) bus, a Video Electronics Standards Association (VESA) local bus, a Peripheral Component Interconnect (PCI) bus, a Universal Serial Bus (USB), etc.

Processing subsystem 1602, which can be implemented as one or more integrated circuits (e.g., a conventional microprocessor or microcontroller), controls the operation of computer system 1600. Processing subsystem 1602 may include one or more processors 1604. Each processor 1604 may include one processing unit 1606 (e.g., a single core processor such as processor 1604-1) or several processing units 1606 (e.g., a multicore processor such as processor 1604-2). In some embodiments, processors 1604 of processing subsystem 1602 may be implemented as independent processors while, in other embodiments, processors 1604 of processing subsystem 1602 may be implemented as multiple processors integrate into a single chip or multiple chips. Still, in some embodiments, processors 1604 of processing subsystem 1602 may be implemented as a combination of independent processors and multiple processors integrated into a single chip or multiple chips.

In some embodiments, processing subsystem 1602 can execute a variety of programs or processes in response to program code and can maintain multiple concurrently executing programs or processes. At any given time, some or all of the program code to be executed can reside in processing subsystem 1602 and/or in storage subsystem 1610. Through suitable programming, processing subsystem 1602 can provide various functionalities, such as the functionalities described above by reference to process 500, process 800, process 1200, process 1500, etc.

I/O subsystem 1608 may include any number of user interface input devices and/or user interface output devices. User interface input devices may include a keyboard, pointing devices (e.g., a mouse, a trackball, etc.), a touchpad, a touch screen incorporated into a display, a scroll wheel, a click wheel, a dial, a button, a switch, a keypad, audio input devices with voice recognition systems, microphones, image/video capture devices (e.g., webcams, image scanners, barcode readers, etc.), motion sensing devices, gesture recognition devices, eye gesture (e.g., blinking) recognition devices, biometric input devices, and/or any other types of input devices.

User interface output devices may include visual output devices (e.g., a display subsystem, indicator lights, etc.), audio output devices (e.g., speakers, headphones, etc.), etc. Examples of a display subsystem may include a cathode ray tube (CRT), a flat-panel device (e.g., a liquid crystal display (LCD), a plasma display, etc.), a projection device, a touch screen, and/or any other types of devices and mechanisms for outputting information from computer system 1600 to a user or another device (e.g., a printer).

As illustrated in FIG. 16, storage subsystem 1610 includes system memory 1612, computer-readable storage medium 1620, and computer-readable storage medium reader 1622. System memory 1612 may be configured to store software in the form of program instructions that are loadable and executable by processing subsystem 1602 as well as data generated during the execution of program instructions. In some embodiments, system memory 1612 may include volatile memory (e.g., random access memory (RAM)) and/or non-volatile memory (e.g., read-only memory (ROM), programmable read-only memory (PROM), erasable programmable read-only memory (EPROM), electrically erasable programmable read-only memory (EEPROM), flash memory, etc.). System memory 1612 may include different types of memory, such as static random access memory (SRAM) and/or dynamic random access memory (DRAM). System memory 1612 may include a basic input/output system (BIOS), in some embodiments, that is configured to store basic routines to facilitate transferring information between elements within computer system 1600 (e.g., during start-up). Such a BIOS may be stored in ROM (e.g., a ROM chip), flash memory, or any other type of memory that may be configured to store the BIOS.

As shown in FIG. 16, system memory 1612 includes application programs 1614, program data 1616, and operating system (OS) 1618. OS 1618 may be one of various versions of Microsoft Windows, Apple Mac OS, Apple OS X, Apple macOS, and/or Linux operating systems, a variety of commercially-available UNIX or UNIX-like operating systems (including without limitation the variety of GNU/Linux operating systems, the Google Chrome® OS, and the like) and/or mobile operating systems such as Apple iOS, Windows Phone, Windows Mobile, Android, BlackBerry OS, Blackberry 10, and Palm OS, WebOS operating systems.

Computer-readable storage medium 1620 may be a non-transitory computer-readable medium configured to store software (e.g., programs, code modules, data constructs, instructions, etc.). Many of the components (e.g., word embedding manager 105, terminology manager 110, entity recognizer 115, unknown word manager 120, and custom tags manager 125) and/or processes (e.g., process 500, process 800, process 1200, and process 1500) described above may be implemented as software that when executed by a processor or processing unit (e.g., a processor or processing unit of processing subsystem 1602) performs the operations of such components and/or processes. Storage subsystem 1610 may also store data used for, or generated during, the execution of the software.

Storage subsystem 1610 may also include computer-readable storage medium reader 1622 that is configured to communicate with computer-readable storage medium 1620. Together and, optionally, in combination with system memory 1612, computer-readable storage medium 1620 may comprehensively represent remote, local, fixed, and/or removable storage devices plus storage media for temporarily and/or more permanently containing, storing, transmitting, and retrieving computer-readable information.

Computer-readable storage medium 1620 may be any appropriate media known or used in the art, including storage media such as volatile, non-volatile, removable, non-removable media implemented in any method or technology for storage and/or transmission of information. Examples of such storage media includes RAM, ROM, EEPROM, flash memory or other memory technology, compact disc read-only memory (CD-ROM), digital versatile disk (DVD), Blu-ray Disc (BD), magnetic cassettes, magnetic tape, magnetic disk storage (e.g., hard disk drives), Zip drives, solid-state drives (SSD), flash memory card (e.g., secure digital (SD) cards, CompactFlash cards, etc.), USB flash drives, or any other type of computer-readable storage media or device.

Communication subsystem 1624 serves as an interface for receiving data from, and transmitting data to, other devices, computer systems, and networks. For example, communication subsystem 1624 may allow computer system 1600 to connect to one or more devices via a network (e.g., a personal area network (PAN), a local area network (LAN), a storage area network (SAN), a campus area network (CAN), a metropolitan area network (MAN), a wide area network (WAN), a global area network (GAN), an intranet, the Internet, a network of any number of different types of networks, etc.). Communication subsystem 1624 can include any number of different communication components. Examples of such components may include radio frequency (RF) transceiver components for accessing wireless voice and/or data networks (e.g., using cellular technologies such as 2G, 3G, 4G, 5G, etc., wireless data technologies such as Wi-Fi, Bluetooth, ZigBee, etc., or any combination thereof), global positioning system (GPS) receiver components, and/or other components. In some embodiments, communication subsystem 1624 may provide components configured for wired communication (e.g., Ethernet) in addition to or instead of components configured for wireless communication.

One of ordinary skill in the art will realize that the architecture shown in FIG. 16 is only an example architecture of computer system 1600, and that computer system 1600 may have additional or fewer components than shown, or a different configuration of components. The various components shown in FIG. 16 may be implemented in hardware, software, firmware or any combination thereof, including one or more signal processing and/or application specific integrated circuits.

Figure 17:
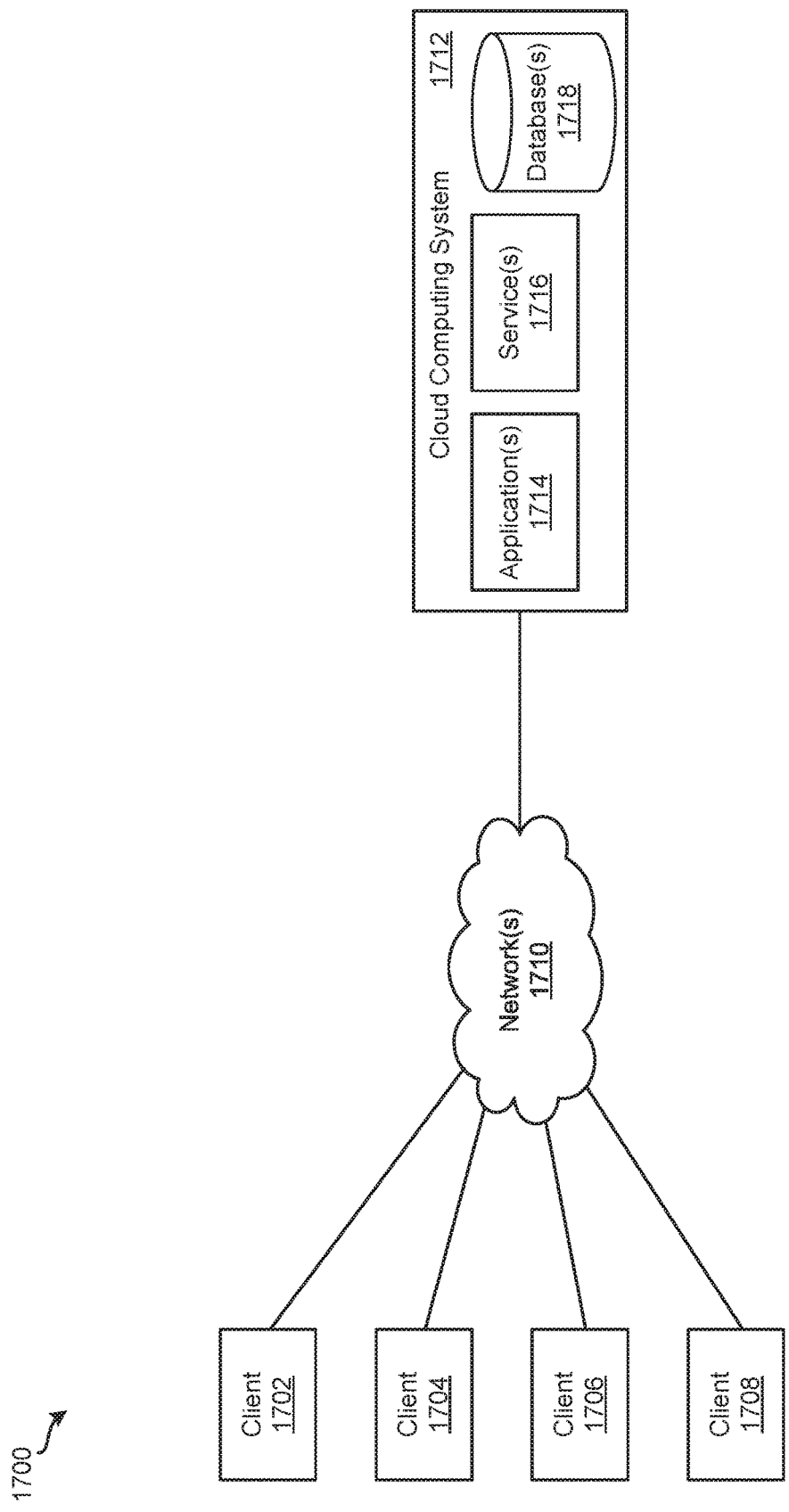
FIG. 17 illustrates an exemplary system, in which various embodiments may be implemented.

FIG. 17 illustrates an exemplary system 1700 for implementing various embodiments described above. For example, cloud computing system of system 1700 may be used to implement computing system 100. As shown, system 1700 includes client devices 1702-1708, one or more networks 1710, and cloud computing system 1712. Cloud computing system 1712 is configured to provide resources and data to client devices 1702-1708 via networks 1710. In some embodiments, cloud computing system 1700 provides resources to any number of different users (e.g., customers, tenants, organizations, etc.). Cloud computing system 1712 may be implemented by one or more computer systems (e.g., servers), virtual machines operating on a computer system, or a combination thereof.

As shown, cloud computing system 1712 includes one or more applications 1714, one or more services 1716, and one or more databases 1718. Cloud computing system 1700 may provide applications 1714, services 1716, and databases 1718 to any number of different customers in a self-service, subscription-based, elastically scalable, reliable, highly available, and secure manner.

In some embodiments, cloud computing system 1700 may be adapted to automatically provision, manage, and track a customers subscriptions to services offered by cloud computing system 1700. Cloud computing system 1700 may provide cloud services via different deployment models. For example, cloud services may be provided under a public cloud model in which cloud computing system 1700 is owned by an organization selling cloud services and the cloud services are made available to the general public or different industry enterprises. As another example, cloud services may be provided under a private cloud model in which cloud computing system 1700 is operated solely for a single organization and may provide cloud services for one or more entities within the organization. The cloud services may also be provided under a community cloud model in which cloud computing system 1700 and the cloud services provided by cloud computing system 1700 are shared by several organizations in a related community. The cloud services may also be provided under a hybrid cloud model, which is a combination of two or more of the aforementioned different models.

In some instances, any one of applications 1714, services 1716, and databases 1718 made available to client devices 1702-1708 via networks 1710 from cloud computing system 1700 is referred to as a "cloud service." Typically, servers and systems that make up cloud computing system 1700 are different from the on-premises servers and systems of a customer. For example, cloud computing system 1700 may host an application and a user of one of client devices 1702-1708 may order and use the application via networks 1710.

Applications 1714 may include software applications that are configured to execute on cloud computing system 1712 (e.g., a computer system or a virtual machine operating on a computer system) and be accessed, controlled, managed, etc. via client devices 1702-1708. In some embodiments, applications 1714 may include server applications and/or mid-tier applications (e.g., HTTP (hypertext transport protocol) server applications, FTP (file transfer protocol) server applications, CGI (common gateway interface) server applications, JAVA server applications, etc.). Services 1716 are software components, modules, application, etc. that are configured to execute on cloud computing system 1712 and provide functionalities to client devices 1702-1708 via networks 1710. Services 1716 may be web-based services or on-demand cloud services.

Databases 1718 are configured to store and/or manage data that is accessed by applications 1714, services 1716, and/or client devices 1702-1708. For instance, storages 130-145 may be stored in databases 1718. Databases 1718 may reside on a non-transitory storage medium local to (and/or resident in) cloud computing system 1712, in a storage-area network (SAN), on a non-transitory storage medium local located remotely from cloud computing system 1712. In some embodiments, databases 1718 may include relational databases that are managed by a relational database management system (RDBMS). Databases 1718 may be a column-oriented databases, row-oriented databases, or a combination thereof. In some embodiments, some or all of databases 1718 are in-memory databases. That is, in some such embodiments, data for databases 1718 are stored and managed in memory (e.g., random access memory (RAM)).

Client devices 1702-1708 are configured to execute and operate a client application (e.g., a web browser, a proprietary client application, etc.) that communicates with applications 1714, services 1716, and/or databases 1718 via networks 1710. This way, client devices 1702-1708 may access the various functionalities provided by applications 1714, services 1716, and databases 1718 while applications 1714, services 1716, and databases 1718 are operating (e.g., hosted) on cloud computing system 1700. Client devices 1702-1708 may be computer system 1600, as described above by reference to FIG. 16. Although system 1700 is shown with four client devices, any number of client devices may be supported.

Networks 1710 may be any type of network configured to facilitate data communications among client devices 1702-1708 and cloud computing system 1712 using any of a variety of network protocols. Networks 1710 may be a personal area network (PAN), a local area network (LAN), a storage area network (SAN), a campus area network (CAN), a metropolitan area network (MAN), a wide area network (WAN), a global area network (GAN), an intranet, the Internet, a network of any number of different types of networks, etc.

The above description illustrates various embodiments of the present invention along with examples of how aspects of the present invention may be implemented. The above examples and embodiments should not be deemed to be the only embodiments, and are presented to illustrate the flexibility and advantages of the present invention as defined by the following claims. Based on the above disclosure and the following claims, other arrangements, embodiments, implementations and equivalents will be evident to those skilled in the art and may be employed without departing from the spirit and scope of the invention as defined by the claims.

What is claimed is:

1. A non-transitory machine-readable medium storing a program executable by at least one processing unit of a device, the program comprising sets of instructions for:
    receiving a set of words;
    determining an embedding for a word in the set of words;
    accessing a knowledge base to retrieve a plurality of entries, each entry comprising a text description of a concept;
    determining, for each entry in the plurality of entries in the knowledge base, an embedding for the entry based on the text description of the concept;
    calculating, for each entry in the plurality of entries in the knowledge base, a first distance value between the embedding for the word in the set of words and the embedding for the entry;
    selecting a defined number of entries from the plurality of entries in the knowledge base having a shortest first distance value;
    determining a subset of the set of words;
    generating an embedding for the subset of the set of words;
    calculating, for each entry in the defined number of entries, a second distance value between the embedding for the subset of the set of words and the embedding for the entry; and
    determining an entry in the plurality of entries in the knowledge base having a text description of a concept that best represents the set of words based on the first distance values for each entry in the plurality of entries and the second distance values for each entry in the defined number of entries.

2. The non-transitory machine-readable medium of claim 1, wherein determining, for each entry in the plurality of entries in the knowledge base, the embedding for the entry based on the text description of the concept comprises determining an embedding for each word in a set of words in the description of the concept, wherein the program further comprises a set of instructions for generating, for each entry in the plurality of entries in the knowledge base, an embedding for the entry based on the determined embeddings for each word in the set of words in the description of the concept.

3. The non-transitory machine-readable medium of claim 2, wherein generating, for each entry in the plurality of entries in the knowledge base, the embedding for the entry comprises:
    calculating an average of the determined embeddings for each word in the set of words in the description of the concept; and
    using the average as the embedding for the entry.

4. The non-transitory machine-readable medium of claim 1, wherein the determined entry in the plurality of entries in the knowledge base is the entry having a shortest first distance value.

5. The non-transitory machine-readable medium of claim 1, wherein the knowledge base is a medical terminology knowledge base, wherein each entry in the knowledge base further comprises a unique identifier associated with the concept described by the text description.

6. The non-transitory machine-readable medium of claim 1, wherein the set of words is raw unstructured text from a document in a medical record of a patient.

7. A method comprising:
    receiving a set of words;
    determining an embedding for a word in the set of words;
    accessing a knowledge base to retrieve a plurality of entries, each entry comprising a text description of a concept;
    determining, for each entry in the plurality of entries in the knowledge base, an embedding for the entry based on the text description of the concept;
    calculating, for each entry in the plurality of entries in the knowledge base, a first distance value between the embedding for the word in the set of words and the embedding for the entry;
    selecting a defined number of entries from the plurality of entries in the knowledge base having a shortest first distance value;
    determining a subset of the set of words;
    generating an embedding for the subset of the set of words; and
    calculating, for each entry in the defined number of entries, a second distance value between the embedding for the subset of the set of words and the embedding for the entry; and
    determining an entry in the plurality of entries in the knowledge base having a text description of a concept that best represents the set of words based on the first distance values for each entry in the plurality of entries and the second distance values for each entry in the defined number of entries.

8. The method of claim 7, wherein determining, for each entry in the plurality of entries in the knowledge base, the embedding for the entry based on the text description of the concept comprises determining an embedding for each word in a set of words in the description of the concept, wherein the method further comprises generating, for each entry in the plurality of entries in the knowledge base, an embedding for the entry based on the determined embeddings for each word in the set of words in the description of the concept.

9. The method of claim 8, wherein generating, for each entry in the plurality of entries in the knowledge base, the embedding for the entry comprises:
   calculating an average of the determined embeddings for each word in the set of words in the description of the concept; and
   using the average as the embedding for the entry.

10. The method of claim 7, wherein the determined entry in the plurality of entries in the knowledge base is the entry having a shortest first distance value.

11. The method of claim 7, wherein the knowledge base is a medical terminology knowledge base, wherein each entry in the knowledge base further comprises a unique identifier associated with the concept described by the text description.

12. The method of claim 7, wherein the set of words is raw unstructured text from a document in a medical record of a patient.

13. A system comprising:
   a set of processing units; and
   a non-transitory machine-readable medium storing instructions that when executed by at least one processing unit in the set of processing units cause the at least one processing unit to:
      receive a set of words;
      determine an embedding for a word in the set of words;
      access a knowledge base to retrieve a plurality of entries, each entry comprising a text description of a concept;
      determine, for each entry in the plurality of entries in the knowledge base, an embedding for the entry based on the text description of the concept;
      calculate, for each entry in the plurality of entries in the knowledge base, a first distance value between the embedding for the word in the set of words and the embedding for the entry;
      select a defined number of entries from the plurality of entries in the knowledge base having a shortest first distance value;
      determine a subset of the set of words;
      generate an embedding for the subset of the set of words; and
      calculate, for each entry in the defined number of entries, a second distance value between the embedding for the subset of the set of words and the embedding for the entry; and
      determine an entry in the plurality of entries in the knowledge base having a text description of a concept that best represents the set of words based on the first distance values for each entry in the plurality of entries and the second distance values for each entry in the defined number of entries.

14. The system of claim 13, wherein determining, for each entry in the plurality of entries in the knowledge base, the embedding for the entry based on the text description of the concept comprises determining an embedding for each word in a set of words in the description of the concept, wherein the instructions further cause the at least one processing unit to generate, for each entry in the plurality of entries in the knowledge base, an embedding for the entry based on the determined embeddings for each word in the set of words in the description of the concept.

15. The system of claim 14, wherein generating, for each entry in the plurality of entries in the knowledge base, the embedding for the entry comprises:
   calculating an average of the determined embeddings for each word in the set of words in the description of the concept; and
   using the average as the embedding for the entry.

16. The system of claim 13, wherein the determined entry in the plurality of entries in the knowledge base is the entry having a shortest first distance value.

17. The system of claim 13, wherein the knowledge base is a medical terminology knowledge base, wherein each entry in the knowledge base further comprises a unique identifier associated with the concept described by the text description.

* * * * *